United States Patent [19]

Zimmermann

[11] Patent Number: 5,612,340
[45] Date of Patent: Mar. 18, 1997

[54] PYRIMIDINEAMINE DERIVATIVES AND PROCESSES FOR THE PREPARATION THEREOF

[75] Inventor: Jürg Zimmermann, Wallbach, Switzerland

[73] Assignee: Ciba-Geigy Corporation, Tarrytown, N.Y.

[21] Appl. No.: 436,345

[22] PCT Filed: Sep. 21, 1994

[86] PCT No.: PCT/EP94/03150

§ 371 Date: May 17, 1995

§ 102(e) Date: May 17, 1995

[87] PCT Pub. No.: WO95/09847

PCT Pub. Date: Apr. 13, 1995

[30] Foreign Application Priority Data

Oct. 1, 1993 [CH] Switzerland ............... 2967/93
Jul. 18, 1994 [CH] Switzerland ............... 2279/94

[51] Int. Cl.⁶ ............... C07D 239/42; A61K 31/505
[52] U.S. Cl. ............... 514/252; 514/275; 544/330; 544/331; 544/332; 544/295; 544/296; 544/238
[58] Field of Search ............... 544/330, 331, 544/332, 295, 296, 238; 514/275, 252

[56] References Cited

U.S. PATENT DOCUMENTS

| | | | |
|---|---|---|---|
| 4,725,600 | 2/1988 | Takaya et al. | 514/269 |
| 4,966,622 | 10/1990 | Rempfler et al. | 544/332 |
| 5,159,078 | 10/1992 | Rempfler et al. | 544/332 |

FOREIGN PATENT DOCUMENTS

| | | |
|---|---|---|
| 0164204 | 12/1985 | European Pat. Off. |
| 0233461 | 8/1987 | European Pat. Off. |
| 337943 | 10/1989 | European Pat. Off. |
| 388838 | 9/1990 | European Pat. Off. |
| 588762 | 3/1993 | European Pat. Off. |
| 564409 | 10/1993 | European Pat. Off. |
| 3436380 | 4/1986 | Germany. |

*Primary Examiner*—John M. Ford
*Attorney, Agent, or Firm*—Marla J. Mathias; Karen G. Kaiser

[57] ABSTRACT

N-phenyl-2-pyrimidineamine derivatives of formula (I) wherein the substituents are as defined in claim 1 are described. Those compounds can be used for example, in the treatment of tumour diseases.

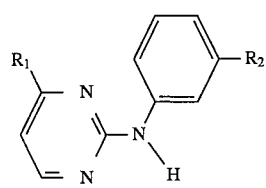

(I)

8 Claims, No Drawings

PYRIMIDINEAMINE DERIVATIVES AND PROCESSES FOR THE PREPARATION THEREOF

This is a 371 of PCT/EP 94/03150, filed Sep. 21, 1994.

The invention relates to N-phenyl-2-pyrimidineamine derivatives, to processes for the preparation thereof, to medicaments comprising those compounds, and to the use thereof in the preparation of pharmaceutical compositions for the therapeutic treatment of warm-blooded animals.

The invention rehtes to N-phenyl-2-pyrimidineamine derivatives of formula I

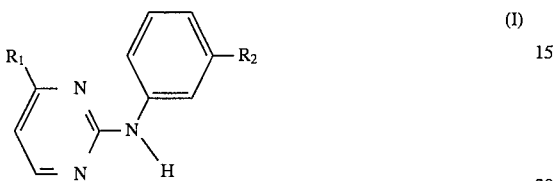

wherein $R_1$ is naphthyl, fiuorenyl, anthracenyl or a substituted cyclic radical, the cyclic radical being bonded to a ring carbon atom in each case and being selected from phenyl, pyridyl, 1H-indolyl, pyrazinyl, thiazolyl, pyrimidinyl, pyridazinyl and imidazolyl, and the substituents of the above-mentioned phenyl radical being selected from hydroxy, halogen, nitro, cyano, unsubstituted or halogen-substituted lower alkoxy, from a radical of formula II —C(=O)—(O)$_m$—R$_3$ (II)

wherein m is 0 or 1 and $R_3$ is hydrogen, benzyl, lower alkyl or amino-lower alkyl wherein the amino group is free, lower alkylated or lower alkanoylated, from a radical of formula III

—C(=O)—N(R$_4$)R$_5$ (III)

wherein $R_4$ and $R_5$ are each independently of the other hydrogen or unsubstituted or amino- or hydroxy-substituted lower alkyl, from a radical of formula IV

—SO$_2$—N(R$_6$)R$_7$ (IV)

wherein $R_6$ and $R_7$ are each independently of the other hydrogen, lower alkyl or amino-lower alkyl, or wherein $R_6$ and $R_7$ together form the bivalent radical —(CH$_2$)$_2$—NH—(CH$_2$)$_2$13 , and from a radical of formula V

—N(R$_8$)R$_9$ (V)

wherein $R_8$ and $R_9$ are each independently of the other lower alkyl, or wherein $R_8$ is hydrogen and $R_9$ is amino or amino-cyclohexyl, or is lower alkyl that is substituted by imidazolyl, guanidyl, lower alkylaminocarbonylamino, amidino, di-lower alkylamino-cyclohexyl, piperazinyl, carboxy, lower alkoxycarbonyl, carbamoyl, N-hydroxy-carbamoyl, hydroxy, lower alkoxy, dihydroxyphosphoryloxy or by formylpiperazinyl, and the substituents of the other above-mentioned cyclic radicals being selected from hydroxy, halogen, cyano, amino-lower alkyl, unsubstituted or halogen-substituted lower alkoxy, phthalimido-substituted lower alkyl, from a radical of the above-mentioned formulae II, III or IV and from a radical of formula VI

—N(R$_{10}$)R$_{11}$ (VI)

wherein $R_{10}$ and $R_{11}$ are each independently of the other hydrogen or lower alkyl, or wherein $R_{10}$ is hydrogen and $R_{11}$ is amino or amino-cyclohexyl, or is lower alkyl substituted by amino, lower alkylamino, di-lower alkylamino, lower alkanoylamino, imidazolyl, guanidyl, lower alkyl-amino-carbonylamino, amidino, di-lower alkylamino-cyclohexyl, piperazinyl, formylpiperazinyl, carboxy, lower alkoxycarbonyl, carbamoyl, N-hydroxy-carbamoyl, hydroxy, lower alkoxy, dihydroxyphosphoryloxy or by glycylamido; and $R_2$ is nitro, fluorine-substituted lower alkoxy or a radical of formula VII —N(R$_{12}$)—C(=X)—(Y)$_n$—R$_{13}$ (VII)

wherein $R_{12}$ is hydrogen or lower alkyl,

X is oxo, thio, imino, N-lower alkyl-imino, hydroximino or O-lower alkyl-hydroximino, Y is oxygen or the group NH, n is 0 or 1, and $R_{13}$ is an aliphatic radical having at least 5 carbon atoms, or an aromatic, aromatic-aliphatic, cycloaliphatic, cycloaliphatic-aliphatic, heterocyclic or heterocyclic-aliphatic radical, and to salts of such compounds having at least one salt-forming group.

Naphthyl $R_1$ is 1-naphthyl or 2-naphthyl.

Anthracenyl $R_1$ is preferably 9-anthracenyl.

Fluorenyl $R_1$ is preferably 2-fluorenyl.

A substituted phenyl radical $R_1$ can have several substituents, but especially not more than 3 and, especially in the case of relatively large substituents, preferably only one substituent, which substituents are principally in the para- (or 4-position) anct/or preferably meta-position (or 3-position). The other above-mentioned substituted cyclic radicals $R_1$ generally have up to two and preferably only one substituent, which is especially in the rneta- or para-position with respect to the bonding site of the cyclic radical $R_1$.

Pyridyl bonded to a ring carbon atom is 2- or preferably 4- or 3-pyridyl, especially 4-pyridyl. In a mono-substituted pyridyt radical $R_1$, the substituent is preferably in the ortho-position with respect to the pyridine nitrogen.

1H-indolyl bonded to a carbon atom of the five-membered ring is 1H-indol-2-yl or preferably 1H-indol-3-yl. In mono-substituted 1H-indolyl, the substituent is preferably in the 1-position, that is to say, at the nitrogen.

Halogen in a radical $R_1$ is preferably chlorine or fluorine.

Halogen-substituted phenyl $R_1$ is preferably 2-, 3- or 4-chloro-phenyl, 2,4-, 3,4- or 2,5- dichloro-phenyl or 2,3,4-trichloro-phenyl Unsubstituted or halogen-substituted lower alkoxy as substituent of a substituted phenyl radical R1 is preferably methoxy, ethoxy or trifiuoro-methoxy.

A radical of formula II is, for example, a radical wherein m is 1 and $R_3$ is hydrogen, that is to say, carboxy.

A radical of formula III is, for example, a radical wherein $R_4$ is hydrogen and $R_5$ is hydrogen, ω-amino-alkyl having 2 or 3 carbon atoms or ω-hydroxy-alkyl having 2 or 3 carbon atoms, that is to say, carbamoyl, 2-amino-ethyl, 2-hydroxy-ethyl, 3-amino-propyl or 3-hydroxy-propyl A radical of formula IV is, for example, a radical wherein $R_6$ is hydrogen and $R_7$ is ω-amino-$C_{2-3}$alkyl or wherein $R_6$ and $R_7$ together form the bivalent radical —$(CH_2)_2$—NH—$(CH_2)_2$—, that is to say, they form a piperazinyl ring together with the nitrogen atom to which $R_6$ and $R_7$ are bonded.

Amino-cyclohexyl $R_9$ or $R_{11}$ is preferably 4-amino-cyclohexyl. Di-lower alkylaminocyclohexyl as the radical $R_9$ or as part of a substituted lower alkyl radical $R_9$ or $R_{11}$ is preferably 4-di-lower alkylamino-cyclohexyl, preferably 4-dimethylamino-cyclohexyl.

Lower alkylamino in a radical $R_9$ or $R_{11}$ is preferably methylamino.

Di-lower alkylamino in a radical $R_9$ or $R_{11}$ is preferably dimethylamino.

Lower alkanoylamino in a radical $R_9$ or $R_{11}$ is preferably acetylamino.

Formyl-piperazinyl in a radical $R_9$ or $R_{11}$ is preferably 4-formyl-piperazinyl.

Lower alkyl $R_9$ substituted by imidazolyl, guanidyl, lower alkylamino-carbonylamino, amidino, di-lower alkylamino-cyclohexyl, piperazinyl, carboxy, lower alkoxycarbonyl, carbamoyl, N-hydroxy-carbamoyl, hydroxy, lower alkoxy, dihydroxyphosphoryloxy or by formylpiperazinyl, or lower alkyl $R_{11}$ substituted by amino, lower alkylamino, di-lower alkylamino, lower alkanoylamino, imidazolyl, guanidyl, lower alkylamino-carbonylamino, amidino, di-lower alkylamino-cyclonexyl, piperazinyl, formylpiperazinyl, carboxy, lower alkoxycarbonyl, carbamoyl, N-hydroxy-carbamoyl, lower alkoxy, dihydroxyphosphoryloxy or by glycylamido is preferably toorio-, di- or tri-methylene substituted in that manner, the substituents preferably being in the ω-position. In addition, hydroxy-substituted lower alkyl $R_9$ or $R_{11}$ is preferably also 2-hydroxy-propyl.

Fluorine-substituted lower alkoxy $R_2$ is lower alkoxy that carries at least one, but preferably several, fluorine substituents, especially trifluoromethoxy or more especially 1,1,2,2-tetrafluoro-ethoxy.

When X is oxo, thio, imino, N-lower alkyl-imino, hydroximino or O-lower alkyl-hydroximino, the group C=X is, in the order mentioned, the radical C=O, C=S, C=N—H, C=N-lower alkyl, C=N—OH or C=N—O -lower alkyl. X is preferably oxo.

n is preferably 0, that is to say, the group Y is not present. Y, if present, is preferably the group NH.

Within the scope of this text, the term "lower" denotes radicals having up to and including 7, preferably up to and including 4, carbon atoms.

Unless otherwise indicated in the context concerned, lower alkyl is preferably methyl or ethyl.

An aliphatic radical R13 having at least 5 carbon atoms preferably has not more than 22 carbon atoms and generally not more than 10 carbon atoms and is such a substituted or preferably unsubstituted aliphatic hydrocarbon radical, that is to say, such a substituted or preferably unsubstituted alkynyl, alkenyl or preferably alkyl radical, such as $C_5$–$C_7$alkyl, for example n-pentyl. An aromatic radical $R_{13}$ has up to 20 carbon atoms and is unsubstituted or substituted, for example naphthyl, such as especially 2-naphthyl, or preferably phenyl, each of which is unsubstituted or substituted, the substituents preferably being selected from cyano, lower alkyl that is unsubstituted or substituted by hydroxy, amino or by 4-methyl-piperazinyl, such as especially methyl, from trifluoromethyl, free, etherified or esterified hydroxy, free, alkylated or acylated amino and from free or esterified carboxy. In an aromatic-aliphatic radical $R_{13}$, the aromatic moiety is as defined above and the aliphatic moiety is preferably lower alkyl, such as especially $C_1$–$C_2$alkyl, that is substituted or preferably unsubsfituted, for example benzyl. A cycloaliphafic radical $R_{13}$ has especially up to 30, principally up to 20 and more especially up to 10 carbon atoms, is mono- or poly-cyclic and is substituted or preferably unsubstituted, for example such a cycloalkyl radical, especially a 5- or 6-membered cycloalkyl radical, such as preferably cyclohexyl. In a cycloaliphafic-aliphafic radical $R_{13}$, the cycloaliphatic moiety is as defined above and the aliphatic moiety is preferably lower alkyl, such as especially $C_1$–$C_2$-alkyl that is substituted or preferably tinsubstituted. A heterocyclic radical $R_{13}$ contains especially up to 20 carbon atoms and is preferably a saturated or unsaturated monocyclic radical having 5 or 6 ring members and from 1 to 3 hetero atoms which are preferably selected from nitrogen, oxygen and sulfur, especially, for example, thienyl or 2-, 3- or 4-pyridyl, or a bi- or tri-cyclic radical, wherein, for example, one or two benzene radicals are fused (annellated) to the mentioned monocyclic radical. In a heterocyclic-aliphatic radical $R_{13}$, the heterocyclic moiety is as defined above and the aliphatic moiety is preferably lower alkyl, such as especially $C_1$–$C_2$ alkyl, that is substituted or preferably unsubstituted.

Etherified hydroxy in a radical $R_{13}$ is preferably lower alkoxy. Esterified hydroxy in a radical $R_{13}$ is preferably hydroxy esterflied by an organic carboxylie acid, such as a lower alkanoic acid, or by a mineral acid, such as a hydrohalic acid, for example lower alkanoyloxy or especially halogen, such as iodine, bromine or especially fluorine or chlorine.

Alkylated amino in a radical $R_{13}$ is, for example, lower alkylamino, such as methylamino, or di-lower alkylamino, such as dimethylamino. Acylated amino is, for example, lower alkanoylamino or benzoylamino.

Esterified carboxy in a radical $R_{13}$ is, for example, lower alkoxycarbonyl, such as methoxycarbonyl.

Salt-forming groups in a compound of formula I are groups or radicals having basic or acidic properties. Compounds having at least one basic group or at least one basic radical, for example a free amirto group, a pyrazinyl radical or a pyridyl radical, can form acid addition salts, for example with inorganic acids, such as hydrochloric acid, sulfuric acid or a phosphoric acid, or with suitable organic carboxylic or surfonic acids, for example aliphatic mono- or di-carboxylic acids, such as trifiuoroacetic acid, acetic acid, propionic acid, glycolic acid, succinic acid, maleic acid, fumaric acid, hydroxymaleic acid, malic acid, tartaric acid, citric acid, oxalic acid or amino acids, such as arginine or lysine, aromatic carboxylic acids, such as benzoic acid, 2-phenoxy-benzoic acid, 2-acetoxy-benzoic acid, salicylic acid, 4-aminosalicylic acid, aromatic-aliphatic carboxylic acids, such as mandelic acid or cinanmic acid, heteroaromatic carboxylic acids, such as nicotinic acid or isonicotinic acid, aliphatic sulfonic acids, such as methane-, ethane- or 2-hydroxy-ethane-sulfonic acid, or aromatic sulfonic acids, for example benzene-, p-oluene- or naphthalene-2-sulfonic acid. If several basic groups are present, mono- or poly-acid addition salts can be formed.

Compounds of formula I having acidic groups, for example a free carboxy group in the radical $R_1$, can form metal or ammonium salts, such as alkali metal or alkaline earth metal salts, for example sodium, potassium, magnesium or calcium salts, or ammonium salts with ammonia or suitable organic amines, such as tertiary monoamines, for example triethylamine or tri(2-hydroxyethyl)amine, or heterocyclic bases, for example N-ethyl-piperidine or N,N'-dimethyl-piperazine.

Compounds of formula I that possess both acidic and basic groups can form internal salts.

For the purpose of isolation or purification and also in the case of the compounds used further as intermediates, it is also possible to use pharmaceutically unacceptable salts. Only the pharmaceutically acceptable non-toxic salts are used therapeutically, however, and those are therefore preferred.

In view of the close relationship between the novel compounds in free form and in the form of their salts, including also salts that can be used as intermediates, for example in the pitcation of the novel compounds or in order to identify those compounds, hereinbefore and hereinafter any reference to the free compounds is to be understood as including also the corresponding salts, where appropriate and expedient.

The compounds of formula I exhibit valuable pharmacological properties: for example, they inhibit the enzyme protein kinase C with a high degree of selectivity. Phospholipid- and calcium-dependent protein kinase C occurs in cells in a number of forms and participates in various fundamental processes, such as signal transmission, proliferation and differentiation, and also the release of hormones and neurotransmitters. The activation of that enzyme is effected either by receptor-mediated hydrolysis of phospholipids of the cell membrane or by direct interaction with certain tumour-promoting active substances. The sensitivity of the cell to receptor-mediated signal transmission can be substantially influenced by modifying the activity of protein kinase C (as a signal transmitter).

Compounds that are capable of influencing the activity of protein kinase C can be used as tumour-inhibiting, antiinflammatory, immunomodulating and antibacterial active ingredients and may even be of value as agents against atherosclerosis and disorders of the cardiovascular system and central nervous system.

Formerly, porcine brain protein kinase C purified in accordance with the procedure described by T. Uchida and C. R. Filburn in J. Biol. Chem. 259, 12311–4 (1984) was used to determine the inhibitory action on protein kinate C, and the inhibitory action on protein kinase C was determined in accordance with the procedure of D. Fabbro et al., Arch. Biochem. Biophys. 239, 102–111 (1985).

The porcine brain protein kinase C formerly used is a mixture of various sub-types (isotypes) of protein kinase C. If pure recombinant isotypes are used instead of porcine brain protein kinase C in the above test it is found that the compounds of formula I inhibit the "conventional" isotype α preferentially whereas the other "conventional" isotypes β-1, β-2 and γ and especially the "non-conventional" isotypes δ, ε and η and the "atypical" isoform ζ are inhibited to a distinctly lesser extent and in some cases hardly at all Recombinant PKC isotypes are cloned, expressed and purified in the following manner:.

The production of various proteins with the aid of baculoviruses, and their cloning and isolation from Sf9 insect cells are carried out as described by M. D. Summers and G. E. Smith, "A manual method for baculovirus vectors and insect cell culture procedure", Texas Agricul. Exptl. Station Bull. (1987), 1555. The construction and isolation of recombinant viruses for the expression of PKC-α (bovine), PKC-β1 (human), PKC-β2 (human) and PKC-γ (human/bovine hybrid) in Sf9 cells are effected in the manner described by Stabel et al. [S. Stabel, M. Liyanage and D. Frith, "Expression of protein kinase C isozymes in insect cells and isolation of recombinant proteins", Meth. Neurosc. (1993)]. The production of the PKC isotypes in Sf9 cells is carried out in the manner indicated by Stabel et al. (see above), and the purification of the enzymes is effected in accordance with the method described in the publication by MeGlynn et al. [E. MeGlynn, J. Liebetanz, S. Reutener, J. Wood, N. B. Lydon, H. Hofstetter, M. Vanek, T. Meyer and D. Fabbro, "Expression and partial characterization of rat protein kine C-δ and protein kinase C-ζ in insect cells using recombinant baculovirus", J. Cell. Biochem. 49, 239–250 (1992)]. For the generation of recombinant PKC-δ (rat), PKC-ε (rat), PKC-ζ (rat) and PKC-η (mouse), and their expression and pitcation, the procedure described by Liyanage et al. ["Protein kinase C group B members PKC-δ, -ε, -ζ and PKC-λ: Comparison of properties of recombinant proteins in vitro and in vivo", Biochem. J. 283, 781–787 (1992)] and McGlynn et al., respectively, (see above) is followed, with the additional feature that the transfer vector pAc360 is used for the expression of PKC-η [V. Luckow and M.D. Summers, "Trends in the development of baculovirus expression", Biotechnology 6, 47–55 (1988)].

The measurement of the activity of the recombinant PKC isotypes obtained by the above method is carried out in the absence of lipid and calcium (co-factors). Protamine sulfate phosphorylated in the absence of co-factors is used as the substrate. The activity of the enzymes reflects the transfer of $^{32}P$ from $\gamma$-$[^{32}P]$-ATP to protamine sulfate. Protamine sulfate is a mixture of polypeptides each comprising four C-terminal arginine residues. Phosphate incorporation is measured under the following conditions: 100 µl of the reaction mixture comprise in final concentrations 20 mM TRIS-HCl pH 7.4, 10 mM Mg[NO$_3$]$_2$, 0.5 mg/ml of protamine sulfate, 10 µM ATP (0.1 µCi γ-$[^{32}P]$-ATP; 10 Ci/mol; Amersham, Little Chalfont, United Kingdom), various concentrations of the inhibitory compounds and 0.5–2.5 U (units: a unit is the amount of enzyme that, in one minute and per milligram of protein, transfers one nanomole of $^{32}P$ from the above-mentioned γ-$[^{32}P]$-ATP to histome H1 [Sigma, type V-S]) of the enzymes. The reaction is started by the addition of the enzymes and transfer at 32° C. The reaction time is 20 minutes. The reaction is then stopped by dripping aliquots of 50 µl onto P81 chromatography paper (Whatman, Maidstone, United Kingdom). After removing unbound γ-$[^{32}P]$-ATP and nucleotide fragments by washing operations as described by J. J. Witt and R. Roskoski, "Rapid protein kinase assay using phospho-cellulose-paper absorption", Anal. Biochem. 66, 253–258 (1975), the substrate phosphorylation is determined by scintillation measurement. In that test, the compounds of formula I inhibit the α-isotype of protein kinase C (PKC) at an IC$_{50}$ of as low as approximately from 0.1 to 5.0 µmol/litre, generally approximately from 0.1 to 1.0 µmol/litre. In contrast, the other isotypes of PKC are generally inhibited only at distinctly higher concentrations (i.e. at concentrations up to more than 300 times higher).

As may be expected purely on the basis of the above-described inhibitory action on protein kinase C, the compounds of formula I exhibit antiproliferative properties which can be demonstrated directly in another test described in the following in which the inhibitory action of the compounds of formula I on the growth of human T24 bladder carcinoma cells is determined. Those cells are incubated in Eagle's minimal essential medium, to which 5% (v/v) foetal calf serum has been added, in a humidified incubator at 37° C. and with 5% by volume of $CO_2$ in the air. The carcinoma cells (1000–1500) are sown in 96-well microtitre plates and incubated overnight under the above-mentioned conditions. The test compound is added in serial dilutions on day 1. The plates are incubated for 5 days under the above-mentioned conditions. During that period the control cultures undergo at least four cell divisions. After incubation, the cells are fixed with 3.3% (w/v) aqueous glutaraldehyde solution, washed With water and stained with 0.05% (weight/volume) aqueous methylene blue solution. After washing, the dye is eluted with 3% (w/v) aqueous hydrochloric acid. The optical density (OD) per well, which is directly proportional to the number of cells, is then measured at 665 nan using a photometer CTitertek multi-slam). The $IC_{50}$ values are calculated with a computer system using the formula $$\frac{OD_{665} \text{ (test) minus } OD_{665} \text{ (start)}}{OD_{665} \text{ (control) minus } OD_{665} \text{ (start)}} \times 100.$$

The $IC_{50}$ values are defined as being the concentration of active ingredient at which the number of cells per well at the end of the incubation period is only 50% of the number of cells in the control cultures. In the case of the compounds of formula I, the $IC_{50}$ values so ascertained are approximately from 0.1 to 10 µmol/litre.

The anti-tumour activity of the compounds of formula I can also be demonstrated in vivo:

Female Balb/c hairless mice with s.c. transplanted human bladder tumours T24 are used to determine the anti-tumour activity. On day 0, with the animals under peroral forene narcosis, approximately 25 mg of a solid turnour are placed under the skin on the animals' left flank and the small incised wound is closed by means of suture clips. On day 6 after the transplantation, the mice are divided at random into groups of 6 animals and treatment commences. The treatment is carried out for 15 days with peroral or intraperitoneal administration once daily of a compound of formula I in dimethyl sulfoxiderrween 80/-sodium chloride solution in the various doses. The turnouts are measured twice a week with a slide gauge and the volume of the tumours is calculated. In that test, the peroral or intraperitoneal administration of a compound of formula I brings about a marked reduction in the average tumour volume in comparison with the untreated control animals.

On the basis of the properties described, the compounds of formula I can be used especially as tumour-inhibiting active ingredients, for example in the treatment of tumours of the bladder and the skin. When the compounds of formula I are used in the treatment of cancer in combination with other chemotherapeutic drugs, they prevent the development of resistance (multidrug resistance) or eliminate an already existing resistance to the other chemotherapeutic drugs. They are also suitable for the other uses mentioned above for protein kinase C modulators and can be used especially in the treatment of disorders responsive to inhibition of protein kinase C.

Some of the compounds of formula I also inhibit the tyrosine kinase activity of the receptor for the epidermal growth factor (EGF). That receptor-specific enzyme activity plays a key role in signal transmission in a large number of mammalian cells, including human ceils, especially epithelial cells, cells of the immune system and cells of the central and peripheral nervous system. in the case of various types of cell, the EGF-induced activation of the receptor-associated tyrosine protein kinase (EGF-R-TPK) is a pre-requisite for cell division and accordingly for the proliferation of a cell population. The addition of EGF-receptor-specific tyrosine kinase inhibitors thus inhibits the replication of those cells.

Inhibition of EGF-receptor-specific tyrosine protein kinase (EGF-R-TPK) can be demonstrated, for example, using the method of E. McGlynn et al., Europ. J. Biochem. 207, 265–275 (1992). The compounds according to the invention inhibit the enzyme activity by 50% (IC50) for example at a concentration of from 0.1 to 10 µM.

The compounds of formula I that inhibit the tyrosine kinase activity of the receptor for the epidermal growth factor (EGF) can accordingly be used, for example, in the treatment of benign or malignant tumottrs. They are able to bring about turmour regression and to prevent metastatic spread and the growth of micrometastases. They can be used especially in the case of epidermal hyperproliferation (psoriasis), in the treatment of neoplasia of epithelial character, for example mastocarcinoma, and in the case of leukaemia. The compounds can also be used in the treatment of disorders of the immune system and inflammation if protein kinases are involved. Furthermore, those compounds of formula I can be used in the treatment of disorders of the central or peripheral nervous system if signal transmission by protein kinases is involved.

The compounds of formula I and salts of such compounds having at least one salt-forming group also inhibit the enzyme $p34^{cdc2}$/cycline $B^{cdcx13}$ kinuse. That kinuse controls, in addition to other cdc2-related kinasea, specific phases of cell division, especially the transition from the $G_1$-phase to the S-phase and more especially the transition from the $G_2$-phase to the M-phase.

In chronological order, the cycle of a eukaryofic cell consists of the interphase and the M-phase. The interphase is accompanied by an increase in the size of the cell. In chronological order, the interphase consists for its part of the $G_1$-phase, the S-phase and the $G_2$-phase. In the $G_1$-phase (G=gap) biosynthetic processes take place in the cell. In the S-phase (synthesis phase) the DNA doubles. The cell then enters the $G_2$-phase which ends with the commencement of mitosis.

In chronological order, the M-phase for its part consists of the division of the cell nucleus (mitosis) and the division of the cyWplasm (cytokinesis).

The above-mentioned inhibition of the enzyme $p34^{cdc2}$/cycline $B^{cdc13}$ kinuse can be demonstrated by the following test:

10 µM 1-methyl-aden;me are used to induce starfish oocytes to enter the M-phase. The oocytes are then frozen in liquid nitrogen and stored at −80° C. If necessary, the oocytes are homogenised and centrifuged, as described in D. Arion et al., Cell 55, 371–378 (1988) and V. Rialet and L. Meijer, Anticancer Res. 11, 1581–1590 (1991). In order to purify the $p34^{cdc2}$/cycline $B^{cdc13}$ kinuse, the supernatant of the oocytes is added to $p9^{CKSbs}$-Sepharose grains prepared from recombinant human protein $p9^{CKShs}$, as described in L. Azzi et al., Eur. J. Biochem. 203, 353–360 (1992). After 30 minutes at 4° C. while being turned constantly, the grains are washed thoroughly and the active $p34^{cdc2}$/cycline $B^{cdc13}$ kinuse is eluted with free protein $p9^{CKShs}$ (3 mg/ml). The eluted kinase is tested using historic H1 as substrate, as described in L. Meijer et al., EMBO J. 8, 2275–2282 (1989) and EMBO J. 10, 1545–1554 (1991). In that test, the compounds of formula I and salts of such compounds having at least one salt-forming group exhibit an inhibiting concentration $IC_{50}$ [µmol/litre] of approximately from 0.1 to 5, generally approximately from 0.2 to 2.

That finding would also lead to the expectation that the compounds of formula I and salts of such compounds having at least one salt-forming group can be used in the treatment of hyperproliferative disorders, such as tumours and psoriasis.

The compounds of formula I also inhibit the production of HIV viruses, as shown by the test below, and can accordingly be used as agents against the immune deficiency disease AIDS. The initial symptoms observed after HIV infection in humans is foilowed by a clinical latency period which can last several years. After that period, the stage known as AIDS occurs and usually progresses to death. The latency period is attributed to several factors: immune response, occlusion of the viruses in lymph nodes or other tissue and entry into a stage of molecular and vital latency in which the infected cells do not complete the viral cell cycle, which is why infectious viruses cannot be produced and the infection cannot spread. That stage of molecular latency has been investigated using cell models, such as the ACH-2 cell line [K. Clouse et al., J. Immunol 142, 431 (1989)] and the U1 cell line [T. Folks et al., J. Immunol. 140, 117 (1988)]. Those cells are infected with HIV-1 viruses, but have only a low content of infectious viruses. If, however, those cells are stimulated with physiologically relevant factors that are known to be increased in AIDS patients, such as tumour necrosis factor, interleukin-6 etc., or with chemical inductors, such as phorbol diesters, for example 13-O-acetyl-12-O-n-tetradecanoyl-phorbol, a massive production of virus follows. The ACH-2 and U1 cells are representatives of two different cell families that are targets for HIV infection, namely lymphocytes and macrophages.

Hitherto, effective prevention of the progression of HIV infection to the outbreak of AIDS has not been possible. Many attempts have been made to prevent virus replication after the outbreak of AIDS, that is to say, in a stage in which viruses are produced on a massive scale. In contrast, the compounds of formula I interfere with cell processes that lead to the activation of latently infected HIV cells without impairing norma/cell processes, such as cell division.

If the above-mentioned U1 or ACH-2 cells are used as a model for virallatency, it can be demonstrated that HIV virus production induced by 13-O-acetyl-12-O-n-tetradeeanoylphorbol or tumour necrosis factor-alpha are effectively inhibited by the compounds of formula I at a concentration of approximately from 0.001 to 1 µmol/litre, for example at 0.03 µmol/litre.

A preferred group comprises compounds of formula I wherein the substituted cyclic radical $R_1$ is selected from phenyl, pyridyl and 1H-indolyl, the phenyl substituents being selected from unsubstituted or fluorine-substituted lower alkoxy, from halogen, nitro, from a radical of formula II wherein m is 1 and $R_3$ is hydrogen, and from a radical of formula III wherein $R_4$ is hydrogen and $R_5$ is hydrogen or amino- or hydroxy-substimted lower alkyl, and the substituents of the other above-mentioned cyclic radicals being selected from hydroxy, halogen, lower alkoxy, from amino- or phthalimido-substituted lower alkyl, from a radical of formula II wherein m is 1 and $R_3$ is hydrogen, from a radical of formula III wherein $R_4$ is hydrogen and $R_5$ is hydrogen or amino- or hydroxy-substituted lower alkyl, and from a radical of formula VI wherein $R_{10}$ is hydrogen and $R_{11}$ is amino or amino-cyclohexyl, or is lower alkyl substituted by amino, di-lower alkylamino, lower alkanoylamino, imidazolyl, guanidyl, lower alkylamino-carbonylamino, amidino, di-lower alkylamino-cyclohexyl, piperazinyl, formyl-piperazinyl or by glycylamido; and $R_2$ is fluorine-substituted lower alkoxy or a radical of formuh VII wherein $R_{12}$ is hydrogen, X is oxo, n is 0 and $R_{13}$ is phenyl, and salts of such compounds having at least one salt-forming group.

Especially preferred are compounds of formula I wherein $R_1$ is naphthyl, 9-anthracenyl, 2-fiuorenyl or a substituted cyclic radical selected from phenyl, pyridyl and 1H-indolyl, the phenyl substituents being selected from $C_{1-2}$alkoxy, chlorine, trifluoromethoxy, from a radical of formula II wherein m is 1 and $R_3$ is hydrogen, from a radical of formula III wherein $R_4$ is hydrogen and $R_5$ is hydrogen or $C_{2-3}$alkyl substituted in the ω-position by amino or by hydroxy, from a radical of formula IV wherein $R_6$ is hydrogen and $R_7$ is 2-amino-ethyl, or $R_6$ and $R_7$ together form the bivalent radical —$(CH_2)_2$—NH—$(CH_2)_2$—, and from a radical of formula V wherein $R_8$ is hydrogen and $R_9$ is $C_{2-3}$alkyl substituted in the ω-position by amino, the pyridyl substituents being selected from hydroxy, chlorine, methoxy, from a radical of formula II wherein m is 1 and $R_3$ is hydrogen, from a radical of formula Ill wherein $R_4$ is hydrogen and $R_5$ is hydrogen or $C_{2-3}$alkyl substituted in the ω-position by amino or by hydroxy, from a radical of formula IV wherein $R_6$ is hydrogen and $R_7$ is 2-amino-ethyl, or $R_6$ and $R_7$ together form the bivalent radical —$(CH_2)_2$—NH—$(CH_2)_2$—, and from a radical of formula VI wherein $R_{10}$ is hydrogen and $R_{11}$ is hydrogen, $C_{1-4}$alkyl, amino, 4-amino-cyclohexyl or 2-hydroxy-propyl, or is $C_{1-4}$-alkyl substituted in the ω-position by amino, dimethylamino, acetylamino, imidazol-1-yl, guanidyl, methylamino-carbonylamino, amidino, 4-dimethylamino-cyclohexyl, piperazin-1-yl, 4-formyl-piperazin-1-yl, carboxy, ethoxycarbonyl, carbamoyl, N-hydroxycarbamoyl, hydroxy, methoxy, dihydroxyphosphoryloxy or by glycylamido, and the 1H-indolyl substituents being selected from $C_{2-3}$alkyl substituted in the ω-position by amino or by phthalimido; and $R_2$ is 1,1,2,2-tetrafluoro-ethoxy or a radical of formula VII wherein $R_{12}$ is hydrogen, X is oxo, n is 0 and $R_{13}$ is phenyl, and salts of such compounds having at least one salt-forming group.

Especially preferred are particularly compounds of formula I wherein $R_1$ is a substituted cyclic radical selected from phenyl, pyridyl and 1H-indolyl, the phenyl substituents being selected from $C_{1-2}$alkoxy, chlorine, trifluoromethoxy, from a radical of formula II wherein m is 1 and $R_3$ is hydrogen, and from a radical of formula III wherein $R_4$ is hydrogen and $R_5$ is hydrogen or $C_{2-3}$alkyl substituted in the ω-position by amino or by hydroxy, the pyridyl substituents being selected from hydroxy, chlorine, methoxy, from a radical of formula II wherein m is 1 and $R_3$ is hydrogen, from a radical of formula III wherein $R_4$ is hydrogen and $R_5$ is hydrogen or $C_{2-3}$aalkyl substituted in the ω-position by amino or by hydroxy, and from a radical of formula VI wherein $R_{10}$ is hydrogen and $R_{11}$ is amino or 4-amino-cyclohexyl, or is $C_{1-4}$alkyl substituted in the ω-position by amino, dimethylamino, acetylamino, imidazol-1-yl, guavidyl, methylaminocarbonylamino, amidino, 4-dimethylamino-cyclohexyl, piperazin-1-yl, 4-formyl-piperazin-1-yl or by glycylamido, and the 1H-indolyl substituents being selected from $C_{2-3}$alkyl substituted in the ω-position by amino or by phthalimido; and $R_2$ is 1,1,2,2-tetrafluoro-ethoxy or a radical of formula VII wherein $R_2$ is hydrogen, X is oxo, n is 0 and $R_{13}$ is phenyl, and salts of such compounds having at least one salt-forming group.

More especially preferred are compounds of formula I wherein $R_1$ is naphthyl or a substituted cyclic radical selected from phenyl, pyridyl and 1H-indolyl, the phenyl substituents being selected from $C_{1-2}$alkoxy, chlorine, tritluoromethoxy, nitro, cyano, from a radical of formula II wherein m is 1 and $R_3$ is hydrogen, and from a radical of formula III wherein $R_4$ is hydrogen and $R_5$ is hydrogen or $C_{2-3}$alkyl substituted in the ω-position by amino or by hydroxy, the pyfidyl subsfituents being in the ortho-position with respect to the pyridine nitrogen and being selected from hydroxy, chlorine, methoxy, aminomethyl, from a radical of formula II wherein m is 1 and $R_3$ is hydrogen, from a radical of formula III wherein $R_4$ is hydrogen and $R_5$ is hydrogen or $C_{2-3}$alkyl substituted in the ω-position by amino or by hydroxy, and from a radical of formula VI wherein $R_{10}$ is hydrogen and $R_{11}$ is amino or 4-amino-cyclohexyl, or is $C_{1-4}$alkyl substituted in the ω-position by amino, dimethylamino, acetylamino, imidazol-1-yl, guanidyl, methylaminocarbonylamino, amidino, 4-dimethylamino-cyclohexyl, piperazin-1-yl, 4-formyl-piperazin-1-yl, glycylamido or by carboxy, and the 1H-indolyl substituents being selected from $C_{2-3}$alkyl substituted in the ω-position by amirto or by phthalimido; and $R_2$ is 1,1,2,2-tetrafluoro-ethoxy or a radical of formuh VII wherein $R_{12}$ is hydrogen, X is oxo, n is 0 and $R_{13}$ phenyl, and salts of such compounds having at least one salt-forming group.

Most preferred are the compounds of formula I described in the Examples and salts of such compounds having at least one salt-forming group.

The compounds of formula I and the salts of such compounds having at least one salt-forming group are prepared in accordance with processes known per se. The process according to the invention is effected as follows:

a) a compound of formula VIII

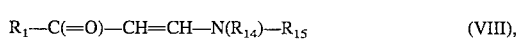

$$R_1-C(=O)-CH=CH-N(R_{14})-R_{15} \quad (VIII),$$

wherein $R_{14}$ and $R_{15}$ are each independently of the other lower alkyl and $R_1$ is as defined above, functional groups present in a compound of formula VIII, with the exception of the groups participating in the reaction, being, if necessary, in protected form, or a salt of such a compound is reacted with a compound of formula IX

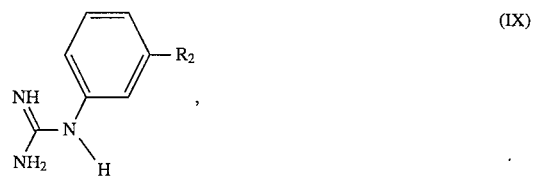

(IX)

wherein $R_2$ is as defined above, functional groups present in a compound of formula IX, with the exception of the guanidino group participating in the reaction, being, if necessary, in protected form, or with a salt of such a compound, and any protecting groups present are removed, or b) for the preparation of a compound of formula I wherein $R_2$ is a radical of formula VII and $R_l$ is as defined above, a compound of formula X

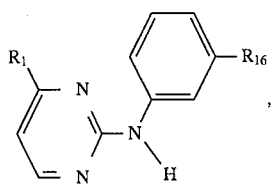

(X)

wherein $R_{16}$ is amino and $R_1$ is as defined above, functional groups present in a compound of formula X, with the exception of the amino group participating in the reaction, being, if necessary, in protected form, is reacted with a compound of formula XI

$$HO-C(=X)-(Y)_n-R_{13} \quad (XI),$$

wherein the substituents and symbols are as defined above, functional groups present in a compound of formula XI, with the exception of the HO—C(=X) group participating in the reaction, being, if necessary, in protected form, or with a reactive derivative of a compound of formula XI, and any protecting groups present are removed, or c) for the preparation of a compound of formula I wherein $R_1$ is pyridyl, pyrazinyl, thiazolyl, pyrimidinyl, pyridazinyl or imidazolyl, each of which is substituted by a radical of formula VI, and $R_2$ is as deemed above, a compound of formula I wherein $R_l$ is pyridyl, pyrazinyl, thiazolyl, pyrimidinyl, pyridazinyl or imidazolyl, each of which is substituted by a leaving group, is reacted with an amine of formula

$$HN(R_{10})R_{11} \quad (XII),$$

wherein the substituents are as dereed above, functional groups present in a compound of formula XII, with the exception of the amirto group participating in the reaction, being, if necessary, in protected form, and any protecting groups present are removed, or d) for the preparation of a compound of formula I wherein $R_1$ is any one of the above-mentioned cyclic radicals substituted by a radical of formula II wherein m is 1 and $R_3$ is hydrogen, or by a radical of formula HI wherein $R_4$ and $R_5$ are each hydrogen, and $R_2$ is as defined above, a compound of formula I wherein $R_1$ is any one of the above-mentioned cyclic radicals substituted by cyano is hydrolysed, or e) for the preparation of a compound of formula I wherein $R_1$ is a pyridyl radical substituted by hydroxy, cyano or by unsubstituted or halogen-substituted lower alkoxy and $R_2$ is as deemed above, in an N-oxido-pyridyl compound of formula XVI

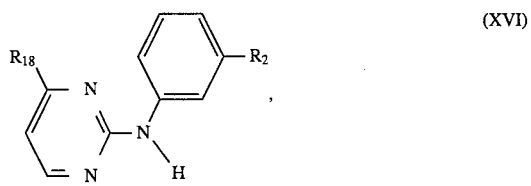

(XVI)

wherein $R_{18}$ is N-oxido-pyridyl bonded to a ring carbon atom and $R_2$ has any one of the above-mentioned meanings, the N-oxido group is converted into a leaving group and the resulting leaving group is removed from the molecule by nucleophilic substitution in the ortho-position with respect to the pyridyl nitrogen using a nucleophile that introduces hydroxy, cyano or unsubstituted or halogen-substituted lower alkoxy, and, if desired, a compound of formuh I obtainable in accordance with any one of Processes a–e is converted into its salt, or an obtainable salt of a compound of formula I is converted into the free compound.

The manner in which the above-mentioned process variants are carried out is explained in detail hereinafter.

General:

The end products of formula I may comprise substiments that can also be used as protecting groups in starting materials for the preparation of other end products of formula I. Within the scope of this text, therefore, unless the context indicates otherwise, only a readily removable group that is not a constituent of the particular end product of formula I desired is referred to as a "protecting group".

Protecting groups and the manner in which they are introduced and removed are described, for example, in "Protective Groups in Organic Chemistry", Plenum Press, London, New York 1973, and in "Methoden der organischen Chemic", Houben-Weyl, 4th edition, Vol. 15/1, Georg-Thieme-Verhg, Stuttgart 1974 and in Theodors W. Greene, "Protective Groups in Organic Synthesis", John Wiley & Sons, New York 1981. A characteristic of protecting groups is that they can be readily removed, that is to say, without undesired secondary reactions taking place, for example by solvolysis, reduction, photolysis or also under physiological conditions.

Hydroxy-protecting groups are, for example, acyl radicals, such as tinsubstituted or substituted, for example halogen-substituted, lower alkanoyl, such as 2,2-dichioroacetyl, or acyl radicals of carbonic acid semiesters, especially tert-butoxycarbonyl, unsubstituted or substituted benzyloxycarbonyl, for example 4-nitrobenzyloxycarbonyl, or diphenylmethoxycarbonyl, or 2-halo-lower alkoxycarbonyl, such as 2,2,2-trichioroethoxycarbonyl, and also trityl or formyl, or organic silyl or stannyl radicals, and also readily removable etherifiying groups, such as tert-lower alkyl, for example tert-butyl, 2-oxa- or 2-thiaaliphatic or-cycloaliphatic hydrocarbon radicals, especially 1-lower alkoxy-lower alkyl or 1-lower alkylthio-lower alkyl, for example methoxymethyl, 1-methoxy-ethyl, 1-ethoxyethyl, methylthiomethyl, 1-methylthioethyl or 1-ethylthioethyl, or 2-oxa- or 2-thia-cycloalkyl having 5 or 6 ring atoms, for example tetrahydrofuryl or 2-tetrahydropyranyl or corresponding thia analogues, and also unsubstituted or substituted 1-phenyl-lower alkyl, such as unsubstituted or substituted benzyl or diphenylmethyl, suitable substituents of the phenyl radicals being, for example, halogen, such as chlorine, lower alkoxy, such as methoxy, and/or nitro.

A protected amino group may, for example, be in the form of a madfly cleavable acylamino, arylmethylamino, etherified mercaptoamino, 2-acyl-lower alk-1-en-yl-amino, silylamino or stannylamino group or in the form of an azido group.

In a corresponding acylamino group, acyl is, for example, the acyl radical of an organic carboxylic acid having, for example, up to 18 carbon atoms, especially of an alkanecarboxylic acid that is unsubstituted or substituted, for example, by halogen or by aryl, or of a benzoic acid that is unsubstituted or substituted, for example, by halogen, lower alkoxy or by vitro, or of a carbonic acid semiester. Such acyl groups are, for example, lower alkanoyl, such as formyl, acetyl or propionyl, halo-lower alkanoyl, such as 2-haloacetyl, especially 2-chloro-, 2-bromo-, 2-iodo-, 2,2,2-trifluoro- or 2,2,2-tfichloro-acetyl, benzoyl that is unsubstituted or substituted, for example, by halogen, lower alkoxy or by vitro, for example benzoyl, 4-chlorobenzoyl, 4-methoxybenzoyl or 4-nitrobenzoyl, or lower alkoxycarbonyl that is branched in the 1-position of the lower alkyl radical or suitably substituted in the 1- or 2-position, especially tenlower alkoxycarbonyl, for example tert-butoxycarbonyl, arylmethoxycarbonyl having one or two aryl radicals that are preferably phenyl that is unsubstituted or toorio- or poly-substituted, for example, by lower alkyl, especially tert-lower alkyl, such as tert-butyl, lower alkoxy, such as methoxy, hydroxy, halogen, for example chlorine, and/or by vitro, such as unsubstituted or substituted benzyloxycarbonyl, for example 4-nitrobenzyloxycarbonyl, or substituted diphenylmethoxycarbonyl, for example benzhydryloxycarbonyl or di(4-methoxyphenyl)methoxycarbonyl, aroylmethoxycarbonyl wherein the aroyl group is preferably benzoyl that is unsubstituted or substituted, for example, by halogen, such as bromine, for example phenacyloxycarbonyl, 2-halo-lower alkoxyearbonyl, for example 2,2,2-trichloroethoxycarbonyl, 2-bromoethoxycarbonyl or 2-iodoethoxycarbonyl, or 2-(trisubstituted silyl)ethoxycarbonyl wherein the substituents are each independently of the others an aliphatic, araliphatic, cycloaliphatic or aromatic hydrocarbon radical that is unsubstituted or substituted, for example, by lower alkyl, lower alkoxy, aryl, halogen or by vitro, and contains up to 15 carbon atoms, such as corresponding unsubstituted or substituted lower alkyl, phenyllower alkyl, cycloalkyl or phenyl, for example 2-tri-lower alkylsilylethoxycarbonyl, such as 2-trimethylsilylethoxycarbonyl or 2-(di-n-butyl-methyl-silyl)-ethoxycarbonyl, or 2-triaryisilylethoxycarbonyl, such as 2-triphenyisilylethoxycarbonyl.

Other acyl radicals suitable as amino-protecting groups are also corresponding radicals of organic phosphoric, phosphortic or phosphinic acids, such as all-lower alkylphosphoryl, for example dimethylphosphoryl, diethylphosphoryl, di-n-propylphosphoryl or diisopropylphosphoryl, dicycloalkylphosphoryl, for example dicyclohexylphosphoryl, unsubstituted or substituted diphenylphosphoryl, for example diphenylphosphoryl, unsubstituted or substituted, for example nitro-substituted, di(phenyl-lower alkyl)phosphoryl, for example dibenzylphosphoryl or di(4-nitrobenzyl)phosphoryl, unsubstimted or substituted phenyloxyphenylphosphonyl, for example phenyloxyphenylphosphonyl, di-lower alkylphosphinyl, for example diethylphosphinyl, or tinsubstituted or substituted diphenylphosphinyl, for example diphenylphosphinyl.

In an arylmethylamino group that is a mono-, di- or, especially, tri-arylmethylamino group, the aryl radicals are especially unsubstituted or substituted phenyl radicals. Such groups are, for example, benzyl-, diphenylmethyl- and, especially, trityl-amino.

An etherfiled mercapto group in an amino group protected by such a radical is especially arylthio or aryl-lower alkylthio wherein aryl is especially phenyl that is unsubstituted or substituted, for example, by lower alkyl, such as methyl or tert-butyl, lower alkoxy, such as methoxy, halogen, such as chlorine, and/or by nitro. A corresponding amino-protecting group is, for example, 4-nitrophenylthio.

In a 2-acyl-lower alk-1-en-1-yl radical that can be used as an amino-protecting group, acyl is, for example, the corresponding radical of a lower alkanecarboxylic acid, of a benzoic acid that is unsubstituted or substituted, for example, by lower alkyl, such as methyl or tert-butyl, lower alkoxy, such as methoxy, halogen, such as chlorine, and/or by nitro, or especially of a carbonic acid semiester, such as a carbonic acid lower alkyl semiester. Corresponding protecting groups are especially 1-lower alkanoyl-prop-1-en-2-yl, for example 1-acetyl-prop-1-en-2-yl, or 1-lower alkoxycarbonyl-prop-1-en-2-yl, for example 1-ethoxycarbonyl-prop-1-en-2-yl.

Preferred amino-protecting groups are acyl radicals of carbonic acid semiesters, especially tert-butoxycarbonyl, benzyloxycarbonyl that is unsubstituted or substituted, for example, as indicated, for example 4-nitro-benzyloxycarbonyl, or diphenylmethoxycarbonyl, or 2-halo-lower alkoxycarbonyl, such as 2,2,2-trichloroethoxycarbonyl, and also trityl or formyl. The removal of the protecting groups that are not constituents of the desired end product of formula I is effected in a manner known per se, for example by solvolysis, especially hydrolysis, alcoholysis or acidolysis, or by means of reduction, especially hydrogenolysis or chemical reduction, as appropriate stepwise or simultaneously.

A protected amino group is freed in a manner known per se and, depending on the nature of the protecting groups, in various manners, preferably by solvolysis or reduction. 2-halo-lower alkoxycarbonylamino (where appropriate after conversion of a 2-bromo-lower alkoxycarbonylamino group into a 2-iodo-lower alkoxycarbonylamino group), aroylmethoxycarbonylamino or 4-nitrobenzyloxycarbonylamino can be cleaved, for example, by treatment with a suitable chemical reducing agent, such as zinc in the presence of a suitable carboxylic acid, such as aqueous acetic acid. Aroylmethoxycarbonylamino can also be cleaved by treatment with a nucleophilic, preferably salt-forming reagent, such as sodium thiophenolate, and 4-nitro-benzyloxycarbonylamino also by treatment with an alkali metal dithionite, for example sodium dithionite. Unsubstituted or substituted diphenylmethoxycarbonylamino, tert-lower alkoxycarbonylamino or 2-tri-substituted silylethoxycarbonylamino can be cleaved by treatment with a suitable acid, for example formic acid or trifiuoroacetic acid, unsubstituted or substituted benzyloxycarbonylamino, for example, by hydrogenolysis, that is to say by treatment with hydrogen in the presence of a suitable hydrogenation catalyst, such as a palladium catalyst, unsubstituted or substituted triarylmethylamino or formylamino, for example, by treatment with an acid, such as a mineral acid, for example hydrochloric acid, or an organic acid, for example formic, acetic or trifluoroacetic acid, where appropriate in the presence of water, and an amino group protected by an organic silyl group can be freed, for example, by hydrolysis or alcoholysis. An amino group protected by 2-haloacetyl, for example 2-chloroacetyl, can be freed by treatment with thiourea in the presence of a base, or with a thiolate salt, such as an alkali metal thiolate, of the thiourea, and subsequent solvolysis, such as alcoholysis or hydrolysis, of the resulting condensation product. An amino group protected by 2-substituted silylethoxycarbonyl can also be converted into the free amino group by treatment with a hydrofluoric acid salt yielding fluoride anions.

A hydroxy group protected by a suitable acyl group, an organic silyl group or by unsubstituted or substituted 1-phenyl-lower alkyl is freed analogously to a correspondingly protected amino group. Hydroxy protected by unsubstituted or substituted 1-phenyl-lower alkyl, for example benzyl, is freed preferably by catalytic hydrogenation, for example in the presence of a palladium-on-carbon catalyst. A hydroxy group protected by 2,2-dichloroacetyl is freed, for example, by basic hydrolysis, and a hydroxy group etherified by tert-lower alkyl or by a 2-oxa- or 2-thia-aliphatic or -cycloaliphatic hydrocarbon radical is freed by acidolysis, for example by treatment with a mineral acid or a strong carboxylic acid, for example trifluoroacetic acid. Hydroxy etherified by an organic silyl radical, for example trimethylsilyl, can also be freed by a hydrofluoric acid salt yielding fluoride anions, for example terfrabutylammonium fluoride.

Process a:

Preferably, $R_{14}$ and $R_{15}$ are each methyl

Free functional groups in a compound of formula VIII, which are advantageously protected by readily removable protecting groups, are especially amino groups in the radical $R_l$ and the imino group of 1H-indolyl. The imino group can be protected, for example, by benzyl.

Free functional groups in a compound of formula IX, which are advantageously protected by readily removable protecting groups, are especially amino groups, but also hydroxy and carboxy groups.

A salt of a compound of formula VIII or IX is preferably an acid addition salt, for example a nitrate or one of the acid addition salts mentioned for the end products of formula I.

The reaction is carried out in a suitable solvent or dispersing agent, for example a suitable alcohol, such as 2-methoxy-ethanol or a suitable lower alkanol, for example isopropanol or isobutanol, at a temperature of from room temperature (approximately 20° C.) to 150° C., for example under reflux. Especially when the compound of formula VIII is used in the form of a salt, that salt is converted into the free compound, preferably/in situ, by the addition of a suitable base, such as an alkali metal hydroxide, for example sodium hydroxide.

The starting material of formula VIII is obtained by reacting a compound of formula XIII

(XIII)

wherein $R_1$ is as defined above, with a compound of formula XIV

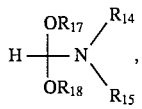
(XIV)

wherein $R_{17}$ and $R_{18}$ are each lower alkyl and the other substituents are as defined above, analogously to the procedure described in the European Patent Application having the publication number 233 461. Typical representatives of a compound of formula XIII are N,N-dimethylformamide dimethylacetal and N,N-dimethylformamide diethylacetal. The reaction is effected while heating the reactants of formulae XKI and XIV, for example for 1–24 hours, in the absence or, if necessary, in the presence of a solvent, at a temperature of approximately from 50° C. to 150° C.

Alternatively, the starting material of formula VIII can also be obtained by reacting a compound of formula XIII with formic acid ethyl ester of the formula H—C(=O)—O—CH$_2$—CH$_3$ and reacting the resulting product with an amine of the formula H—N($R_{14}$)—$R_{15}$ wherein the substituents are as defined above.

The starting material of formula IX is obtained in the form of an acid addition salt by reacting an aniline derivative of formuh XV

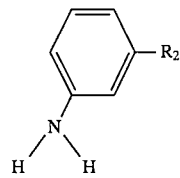
(XV)

wherein $R_2$ is as defined above, with cyanamide (NC—NH$_2$). The reaction is effected in a suitable solvent or dispersing agent, for example a suitable alcohol, for example a suitable lower alkanol, such as ethanol, for example α) in the presence of equimolar amounts of the salt-forming acid, for example nitric acid, or β) in the presence of a clear, for example 60%, excess of a mineral acid, such as hydrochloric acid, an ammonium salt of the desired salt-forming acid, for example ammonium nitrate, being added when the reaction is complete, at a temperature of from room temperature to 150° C., for example under reflux.

Process b:

Free functional groups in a compound of formula X or XI, which are advantageously protected by readily removable protecting groups, are especially amino groups but also hydroxy and carboxy groups which are not to participate in the desired reaction, for example amino in the radical $R_1$.

A reactive derivative of a compound of formula XI wherein X is oxo is especially a reactive (activated) ester, a reactive anhydride or a reactive cyclic amide. The same applies to derivatives wherein X has any one of the other above-mentioned meanings.

Reactive (activated) esters of an acid of formula XI are especially esters unsaturated at the linking carbon atom of the esterifying radical, for example of the vinyl ester type, such as vinyl esters themselves (which can be obtained, for example, by transesterifying a corresponding ester with vinyl acetate; activated vinyl ester method), carbamoyl vinyl esters (which can be obtained, for example, by treating the corresponding acid with an isoxazolium reagent; 1,2-oxazolium or Woodward method), or 1-lower alkoxyvinyl esters (which can be obtained, for example, by treating the corresponding acid with a lower alkoxyacetylene; ethoxyacetylene method), or esters of the amidino type, such as N,N'-di-substituted amidino esters (which can be obtained, for example, by treating the corresponding acid with a suitable N,N'-di-substituted carbodiimide, for example N,N'-dicyclohexylcarbodiimide; carbo diimide method), or N,N-di-substituted amidino esters (which can be obtained, for example, by treating the corresponding acid with an N,N-di-substituted cyanamide; cyanamide method), suitable aryl esters, especially phenyl esters suitably substituted by electron-attracting substituents (which can be obtained, for example, by treating the corresponding acid with a suitably substituted phenol, for example 4-nitrophenol, 4-methylsulfonyl-phenol, 2,4,5-trichlorophenol, 2,3,4,5,6-pentachlorophenol or 4-phenyldiazophenol, in the presence of a condensation agent, such as N,N'-dicyclohexylcarbodmide; activated aryl esters method), cyanomethyl esters (which can be obtained, for example, by treating the corresponding acid with chloroacetonitrile in the presence of a base; cyanomethyl esters method), thio esters, especially unsubstituted or substituted, for example nitro-substituted, phenylthio esters (which can be obtained, for example, by treating the corresponding acid with unsubstituted or substituted, for example nitro-substituted, thiophenols, inter alia by the anthydride or carbodiimide method; activated thiol esters method), amino or amido esters (which can be obtained, for example, by treating the corresponding acid with an N-hydroxy-amino or N-hydroxy-amido compound, for example N-hydroxy-succinimide, N-hydroxy-piperidine, N-hydroxy-phthaliraide or 1-hydroxy-benzotriazole, for example by the anhydride or carbodiimide method; activated N-hydroxy esters method) or silyl esters (which can be obtained, for example, by treating the corresponding acid with a silylating agent, for example hexamethyldisilazane, and which react readily with hydroxy groups but not with amino groups).

Anhydrides of an acid of formula XI may be symmetric or preferably mixed anhydrides of those acids, for example anhydrides with inorganic acids, such as acid halides, especially acid chlorides (which can be obtained, for example, by treating the corresponding acid with thionyl chloride, phosphorus pentachloride or oxalyl chloride; acid chloride method), azides (which can be obtained, for example, from a corresponding acid ester by way of the corresponding hydrazide and treatment thereof with nitrous acid; azide method), anhydrides with carbonic acid semi-derivatives, such as with corresponding esters, for example carbonic acid lower alkyl semiesters (which can be obtained, for example, by treating the corresponding acid with haloformic acid lower alkyl esters, such as chloroformic acid lower alkyl esters, or with a 1-lower alkoxycarbonyl-2-1-lower alkoxy-1,2-dihydroquinoline, for example 1-lower alkoxycarbonyl-2-ethoxy-1,2-dihydroquinoline; mixed O-alkylcarbonic acid anhydrides method), or anhydrides with dihalogenated, especially dichlorinated, phosphoric acid (which can be obtained, for example, by treating the corresponding acid with phosphorus oxychloride; phosphorus oxychloride method), or anhydrides with organic acids, such as mixed anthydrides with organic carboxylic acids (which can be obtained, for example, by treating the corresponding acid with an unsubstituted or substituted lower alkane- or phenylalkane-carboxylic acid halide, for example phenylacetic acid chloride, pivalic acid chloride or trifluoroacetic acid chloride; mixed carboxylic acid anhydrides method) or with organic sulfonic acids (which can be obtained, for example, by treating a salt, such as an alkali metal salt, of the corresponding acid with a suitable organic sulfonic acid halide, such as a lower alkane- or aryl-sulfonic acid chloride, for example methane- or p-toluene-sulfonic acid chloride; mixed sulfonic acid anhydrides method) and symmetric anhydrides (which can be obtained, for example, by condensing the corresponding acid in the presence of a carbodiimide or 1-diethylaminopropyne; symmetric anhydrides method).

Suitable cyclic amides are especially amides having five-membered diazacycles of aromatic character, such as amides with imidazoles, for example imidazole (which can be obtained, for example, by treating the corresponding acid with N,N'-carbonyldiimidazole; imidazolide method), or pyrazoles, for example 3,5-dimethylpyrazole (which can be obtained, for example, by way of the acid hydrazide by treatment with acetylacetone; pyrazolide method).

Derivatives of acids of formula XI that are used as acylating agents can also be formed in situ. For example, N,N'-di-substituted amidino esters can be formed in situ by reacting a mixture of the starting material of formula X and the acid used as acylating agent in the presence of a suitable N,N-di-substituted carbodiimide, for example N,N'-dicyclohexylcarbodiimide. In addition, amino or amido esters or amido esters of the acids used as acylating agents can be formed in the presence of the starting material of formula X to be acylated, by reacting a mixture of the corresponding acid and amino starting materials in the presence of an N,N'-di-substituted carbodiimide, for example N,N'-dicyclohexylcarbodiimide, and of an N-hydroxy-amine or N-hydroxy-amide, for example N-hydroxysuccinimide, where appropriate in the presence of a suitable base, for example 4-dimethylaminopyridine.

The reaction is preferably carried out by reacting a reactive carboxylic acid derivative of a. compound of formula XI with a compound of formula X, the amino or hydroxy group participating in the reaction being in free form.

The reaction can be carried out in a manner known per se, the reaction conditions depending especially upon whether and how the carboxy group of the acylating agent has been activated, generally in the presence of a suitable solvent or diluent or a mixture thereof, and, if necessary, in the presence of a condensation agent which, for example when the carboxy group participating in the reaction is in the form of an anhydride, may also be an acid-binding agent, with cooling or heating, for example in a temperature range of from approximately −30° C. to approximately +150° C., especially approximately from 0° C. to +100° C., preferably from room temperature (approximately +20° C.) to +70° C., open or closed reaction vessel and/or in the atmosphere of an inert gas, for example nitrogen. Customary condensation agents are, for example, carbodiimides, for example N,N'-diethyl-, N,N'-dipropyl-, N,N'-dicyclohexyl- or N-ethyl-'-(3-dimethylaminopropyl)-carbodiimide, suitable carbonyl compounds, for example carbonyldiimidazole, or 1,2-oxazolium compounds, for example 2-ethyl-5-phenyl-1,2-oxazolium-3'-sulfonate and 2-tert-butyl-5-methyl-isoxazolium perchlorate, or a suitable acylamino compound, for example 2-ethoxy-1-ethoxycarbonyl-1,2-dihydroquinoline. Customary acid-binding condensation agents are, for example, alkali metal carbonates or hydrogen carbonates, for example sodium or potassium carbonate or hydrogen carbonate (customafily together with a sulfate), or organic bases, such as customarily pyridine or sterically hindered tri-lower alkylamines, for example N,N-dftsopropyl-N-ethylamine.

The starting material of formula X is obtained by reducing the nitro group(s) in a compound of formula I wherein $R_2$ is nitro. The reduction may be carried out, for example, by catalytic hydrogenation in a suitable solvent, such as a suitable acyclic or cyclic ether, such as in tetrahydrofuran. The hydrogenation catalyst used is preferably palladium/activated carbon (5%) and the hydrogenation is in that case preferably carried out under normal pressure.

Process c:

A leaving group is reactive esterified hydroxy, for example hydroxy esterified by a strong inorganic or organic acid, such as by a mineral acid, for example a hydrohalic acid, such as hydrochloric, hydrobromic or hydriodic acid, also sulfuric acid or a sulfuryl halide, for example sulfuryl fluoride, or by a strong organic sulfonic acid, such as a lower alkanesulfonic acid that is unsubstituted or substituted, for example, by halogen, such as fluorine, or an aromatic sulfonic acid, for example a benzenesulfonic acid that is unsubstituted or substituted by lower alkyl, such as methyl, halogen, such as bromine, and/or by nitro, for example a methanesulfonic, trifluoromethanesulfonic or p-toluenesulfonic acid. A preferred leaving group is halogen, such as, especially, chlorine.

The reaction is preferably carried out in the presence of an excess of the amine of formula XII, which can, where appropriate, also be used as solvent, and, if necessary, in the presence of an inert solvent, such as dimethyl sulfoxide, at a temperature of from room temperature to +150° C., for example at 100° C.

Process d:

The hydrolysis of cyano to carbamoyl can be carried out in the presence of a suitable weak base, such as an alkali metal carbonate, for example sodium carbonate. In order to prevent the hydrolysis from continuing partially to carboxy, it is recommendable to carry out the hydrolysis with hydrogen peroxide in the presence of a suitable olefin, such as preferably a lower alkene, for example 1-hexene, in the presence of an alkali metal carbonate, for example sodium carbonate, in a suitable solvent, such as an alcohol, such as preferably ethanol, at room temperature.

The hydrolysis of cyano to carboxy is carried out in a suitable solvent, such as an alcohol, such as ethanol, for example in the presence of a suitable base, such as aqueous sodium hydroxide solution, at temperatures of from room temperature to +150° C., for example at 60° C.

Process e:

The conversion of the N-oxido group into a leaving group is effected, for example, by reaction with a suitable reactive carboxylic or sulfonic acid derivative, for example with a suitable lower alkanoic acid chloride, lower alkanoic acid anhydride, such as acetic arthydride, N,N-dimethyl-carbamoyl chloride, toluenesulfonyl chloride, methanesulfonyl chloride or trifluoromethanesulfonyl chloride. A nucleophile that introduces cyano is, for example, a suitable silyl cyanide, such as tri-lower alkyl-silyl cyanide, for example trimethyisilyl cyanide. A nucleophile that introduces lower alkoxy or halogen-substituted lower alkoxy is, for example, a corresponding lower alkanol, or a suitable metal salt, such as, for example, an alkali metal salt, thereof, that is to say, a corresponding lower alkanolate. Hydroxy can be introduced, for example, by reacting a compound of formula XVI with a suitable acid arthydride and hydrolysing the resulting intermediate. Process e is carried out in a suitable solvent, such as acetonitrile, at temperatures of approximately from 0° C. to 150° C., preferably approximately from room temperature to 100° C.

The starting material of formula XVI is obtained by oxidising a corresponding pyridyl compound with a suitable oxidising agent, such as a suitable peracid, for example a suitable perbenzoic acid, such as especially m-chloro-perbenzoic acid, in an inert solvent, such as methylene chloride, at room temperature.

Acid addition salts of compounds of formula I are obtained in customary manner, for example by treatment with an acid or a suitable anion exchange reagent.

Acid addition salts can be converted in customary manner into the free compounds, for example by treatment with a suitable basic agent.

Mixtures of isomers can be separated into the individual isomers in a manner known per se, for example by fractional crystallisation, chromatography, etc.

The processes described above, including the processes for removing protecting groups and the additional process measures are, unless otherwise indicated, carried out in a manner known per se, for example in the presence or absence of preferably inert solvents or diluents, if necessary in the presence of condensation agents or catalysts, at reduced or elevated temperature, for example in a temperature range of from approximately −20° C. to approximately 150° C., especially from approximately 0° C. to approximately +70° C., preferably from approximately +10° C. to approximately +50° C., principally at room temperature, in a suitable vessel and, if necessary, in an inert gas atmosphere, for example a nitrogen atmosphere.

Taking into account all the substituents in the molecule, if necessary, for example if readily hydrolysable radicals are present, especially mild reaction conditions are to be used, such as short reaction times, the use of mild acidic or basic agents in low concentration, stoichiometric ratios, and the selection of suitable catalysts, solvents, temperature conditions and/or pressure conditions.

The invention relates also to those forms of the process in which a compound obtainable as intermediate at any stage of the process is used as starting material and the remaining process steps are carried out or the process is discontinued at any stage or a starting material is formed under the reaction conditions or is used in the form of a reactive derivative or salt. The starting materials used are preferably those which, according to the process, result in the compounds described above as being especially valuable.

The present invention relates also to novel starting materials and/or intermediates and to processes for the preparation thereof. The starting materials used and the reaction conditions chosen are preferably such that the compounds described in this Application as being especially preferred are obtained.

The invention relates also to a method of treating warm-blooded animals suffering from a tumour disease, which method comprises administering to warm-blooded animals requiring such treatment an amount that is effective in inhibiting tumours of a compound of formula I or of a pharmaceutically acceptable salt thereof. The invention relates also to the use of a compound of formula I or of a pharmaceutically acceptable salt thereof in the inhibition of protein kinase C in warm-blooded animals or in the preparation of pharmaceutical compositions for use in the therapeutic treatment of the human or animal body. Depending on the species, age, individual condition, mode of administration and the particular clinical picture, effective doses, for example daily doses of approximately 1–1000 mg, especially 50–500 mg, are administered to a warm-blooded animal of approximately 70 kg body weight.

The invention relates also to pharmaceutical compositions comprising an effective amount, especially an mount effective in the prophylaxis or treatment of one of the above-mentioned disorders, of the active ingredient together with pharmaceutically acceptable carriers that are suitable for topical, enteral, for example oral or rectal, or parenteral administration and that may be inorganic or organic, solid or liquid. There are used for oral administration especially tablets or gelatin capsules that comprise the active ingredient together with diluents, for example lactose, dextrose, sucrose, mannitol, sorbitol, cellulose and/or glycerol, and/or lubricants, for example silica, talc, stearic acid or salts thereof, such as magnesium or calcium stearate, and/or polyethylene glycol Tablets may also comprise binders, for example magnesium aluminium silicate, starches, such as corn, wheat or rice starch, gelatin, methylcellulose, sodium carboxymethylcellulose and/or polyvinylpyrrolidone, and, if desired, disintegrators, for example starches, agar, alginic acid or a salt thereof, such as sodium alginate, and/or effervescent mixtures, or adsorbents, dyes, flavourings and sweeteners. It is also possible to use the pharmacologically active compounds of the present invention in the form of parenterally administrable compositions or in the form of infusion solutions. Such solutions are preferably isotonic aqueous solutions or suspensions which, for example in the case of lyophilised compositions that comprise the active ingredient alone or together with a carrier, for example mannitol, can be made up prior to use. The pharmaceutical compositions may be sterilised and/or may comprise excipients, for example preservatives, stabilisers, wetting agents and/or emulsifiers, solubilisers, salts for regulating the osmotic pressure and/or buffers. The present pharmaceutical compositions, which may, if desired, comprise other pharmacologically active substances, such as antibiotics, are prepared in a manner known per se, for example by means of conventional mixing, granulating, confectioning, dissolving or lyophilsing processes, and comprise approximately from 1% to 100%, especially from approximately 1% to approximately 20%, active ingredient(s).

The following Examples illustrate the invention without limiting it in any way. The $R_f$ values are determined on silica gel thin-layer plates (Merck, Darmstadt, Gemany). The ratio of the eluants in the eluant mixtures used is indicated in pans by volume (v/v) and temperatures are indicated in degrees Celsius.

Abbreviations:
DMF: dimethylformamide
DMSO: dimethyl sulfoxide
FAB-MS: Fast Atom Bombardment Mass Spectrum
HV: high vacuum
rotovapor: rotary evaporator
RT: room temperature
h: hour(s)
THF: tetrahydrofuran

EXAMPLE 1

1189.4 mg (0.75 mmol) of 3-(1,1,2,2-tetrafluoro-ethoxy)-phenyl-guanidine nitrate are added to a solution of 200 mg (0.75 mmol) of 3-dimethylamino-1-(3,4,5-trimethoxy-phenyl)-2-propen-1-one in 11.5 ml of 1-propanol. After the addition of 33.2 mg (0.83 mmol) of sodium hydroxide, the reaction mixture is boiled under reflux for 23 hours. After cooling to RT, the reaction product is isolated by filtration and washed with 1-propanol and water. After drying at 60° C. under HV, N-[3-(1,1,2,2-tetrafluoro-ethoxy)-phenyl]-4-(3,4,5-trimethoxyphenyl)-2-pyrimidineamine is obtained; $R_f$=0.75 (methylene chloride:methanol=9:1), FAB-MS: 454 ($M^+$+1), m.p. 132° C.

The starting material is obtained in the following manner:

Stage 1.1: 10.1 g (240 mmol) of cyanamide (50% in water) are added to a suspension of 25.2 g (120 mmol) of 3-(1,1,2,2-tetrafluoro-ethoxy)-aniline in 125 ml of ethanol. 16.3 ml of hydrochloric acid (conc., 192 mmol) are then added to the brown solution and the reaction mixture is heated under reflux for 19 h. After cooling to RT, the reaction mixture is concentrated under reduced pressure and the residue is dissolved in 80 ml of water. After the addition of 19.2 g (240 mmol) of ammonium nitrate, the product is isolated by filtration, then washed with water and dried at 60° under I-HV. 3-(1,1,2,2-tetrafluoro-ethoxy)-phenyl-guanidine nitrate is obtained; m.p. 132°–14133°.

Stage 1.2: 0.5 g (2.38 mmol) of 3,4,5-trimethoxyacetophenone is stirred in 2.7 ml of dimethylformamide diethylacetal for 96 h at 110°. After cooling to 0°, filtering and drying, 3-dimethylamino-1-(3,4,5-trimethoxy-phenyl)-2-propen-1-one is obtained; $^1$H-NMR (DMSO): 2.9 (3H,s), 3.1 (3H,s), 3.7 (3H,s), 3.85 (6H,s), 5.83 (1H,d), 7.19 (2H,s), 7.7 (1H,d).

EXAMPLE 2

21.28 g (84.7 mmol) of 3-(1,1,2,2-tetrafluoro-ethoxy)-phenyl-guanidine nitrate are added to a solution of 17.4 g (84.7 mmol) of 3-dimethylamino-1-(3-methoxy-phenyl)-2-propen-1-one in 100 ml of 2-propanol. After the addition of 3.72 g (93.2 mmol) of sodium hydroxide, the reaction mixture is boiled under reflux for 21.3 h. After cooling to RT, the product is isolated by filtration and washed with 1-propanol and water. After drying at 60° under HV, N-[3-(1,1,2,2-tetrafluoro-ethoxy)-phenyl]-4-(3-methoxy-phenyl)-2-pyrimidineamine is obtained; $R_f$=0.7 (methylene chloride:methanol =9:1), FAB-MS: 397 ($M^+$+1), m.p. 103°–104°.

The starting material is obtained in the following manner:

Stage 2.1: 0.5 g (3.3 mmol) of 3-methoxyacetophenone is stirred in 3.8 ml of dimethylformanide diethylacetal for 4.5 h at 110°. After concentration using a rotovapor and chromatography (methylene chloride:methanol=98:2), 3-dimethylamino-1-(3-methoxy-phenyl)-2-propen-1-one is obtained; $^1$H-NMR (DMSO): 2.9 (3H, s), 3.1 (3H,s), 3.8 (3H,s), 5.8 (1H,d), 7.05 (1H,d), 7.4 (3H,m), 7.7 (1H,d).

EXAMPLE 3

539 mg (2.15 mmol) of 3-(1,1,2,2-tetrafluoro-ethoxy)-phenyl-guanidine nitrate are added to a solution of 450 mg (2.15 mmol) of 3-dimethylamino-1-(4-chloro-phenyl)-2-propen-1-one in 5.5 ml of 2-propanol. After the addition of 94.5 mg (2.36 mmol) of sodium hydroxide, the reaction mixture is boiled under reflux for 29 h. After cooling to RT, the product is isolated by filtration and washed with 1-propanol and water. After drying at 60° under HV, N-[3-(1,1,2,2-tetrafluoro-ethoxy)-phenyl]-4-(4-chloro-phenyl)-2-pyrimidineamine is obtained; $R_f$=0.45 (methylene chloride:methanol =98:2), MS: 397 ($M^+$), m.p. 133°–135°.

The starting material is obtained in the following manner:

Stage 3.05 g (3.23 mmol) of 4-chloroacetophenone are stirred in 3.6 ml of dimethylformamide diethylacetal for 17.5 h at 110°. After cooling, precipitation is effected with hexane and the precipitate is isolated by filtration and dried. 3-dimethylamino-1(4-chloro-phenyl)-2-propen-1-one is obtained; $^1$H-NMR (DMSO): 2.9 (3H,s), 3.1 (3H,s), 5.8 (1H,d), 7.5 (2H,m), 7.75 (1H,d), 7.95 (2H,m).

EXAMPLE 4

926.1 mg (3.69 mmol) of 3-(1,1,2,2-tetrafluoro-ethoxy)-phenyl-guanidine nitrate are added to a solution of 801.1 mg (3.69 mmol) of 3-dimethylamino-1-(3-ethoxy-phenyl)-2-propen-1-one in 10 ml of 2-propanol. After the addition of 162.2 mg (4.05 mmol) of sodium hydroxide, the reaction mixture is boiled under reflux for 20 h. After cooling to RT, the reaction product is isolated by filtration and washed with 1-propanol, ethyl acetate and water. After chromatography (hexane:ethyl acetate=7:3), N-[3-(1,1,2,2-tetrafluoro-ethoxy)-phenyl]-4-(3-ethoxy-phenyl)-2-pyrimidineamine is obtained; $R_f$=0.72 (methylene chloride:methanol=98:2), m.p. 88°–96°.

The starting material is obtained in the following manner:

Stage 4.1: 0.625 mg (3.67 mmol) of 3-hydroxy-acetophenone is stirred in 4.0 ml of dimethylformamide diethylacetal for 21 h at 110°. After cooling, filtering, washing with hexane and drying at 60° under HV, 3-dimethylamino-1-(3-ethoxy-phenyl)-2-propen-1-one is obtained; $^1$H-NMR (DMSO): 1.35 (3H,t), 2.9 (3H,s), 3.1 (3H,s), 4.1 (2H,q), 5.8 (1H,d), 7.05 (1H,d), 7.4 (3H,m), 7.7 (1H,d).

EXAMPLE 5

553 mg (2.2 mmol) of 3-(1,1,2,2-tetrafluoro-ethoxy)-phenyl-guanidine nitrate are added to a solution of 570.7 mg (2.2 mmol) of 3-dimethylamino-1-(3-trifluoro-methoxy-phenyl)-2-propen-1-one in 6 ml of 2-propanol. After the addition of 97 mg (2.42 mmol) of sodium hydroxide, the reaction mixture is boiled under reflux for 30 h. After cooling to RT, the product is isolated by filtration and washed with 1-propanol and water. After drying at 60° under HV, N-[3-(1,1,2,2-tetrafluoro-ethoxy)-phenyl]-4-(3-tri-fluoromethoxy-phenyl)-2-pyrimidineamine is obtained; $R_f$=0.77 (methylene chloride:methanol=98:2); FAB-MS: 448 ($M^+$+ 1), m.p. 98°–100°.

The starting material is obtained in the following manner:

Stage 5.1: 0.51 g (2.45 mmol)of 3-trifluoromethoxy-acetophenone is stirred in 2 ml of dimethylformamide diethylacetal for 23 h at 110°. After concentration using a rotovapor and chromatography (toluene:acetone=95:5), 3-dimethylamino-1-(3-trifluoromethoxyphenyl)-2-propen-1-one is obtained; $^1$H-NMR (DMSO): 2.9 (3H,s), 3.1 (3H,s), 5.9 (1H,d), 7.5–7.8 (4H,m), 8.0 (1H,d).

EXAMPLE 6

100 mg (0.25 mmol) of N-[3-(1,1,2,2-tetrafluoro-ethoxy)-phenyl]-4-(2-chloro-4-pyridyl)-2-pyrimidineamine are dissolved in 1 ml of dimethyl sulfoxide, and 0.2 ml of ethylenediamine is added. After stirring for 22 h at 100°, the reaction mixture is concentrated and chromatographed (methylene chloride:methanol:concentrated ammonia solution=90:10:1). N-[3-(1,1,2,2-tetrafluoro-ethoxy)-phenyl]-4-[2-(2-amino-ethyl-amino)-4-pyridyl]-2-pyrimidineamine is obtained; FAB-MS: 423 (M$^+$+H), $R_f$=0.1 (methylene chloride:methanol:concentrated ammonia solution=90:10:1).

The starting material is obtained in accordance with Example 21.

EXAMPLE 7

Analogously to Example 6 there is obtained from 100 mg (0.251 mmol) of N-[3-(1,1,2,2-tetrafluoro-ethoxy)-phenyl]-4-(2-chloro-4-pyridyl)-2-pyrimidineamine and 2 ml of 3-dimethylamino-1-propylamine N-[3-(1,1,2,2-tetrafluoro-ethoxy)-phenyl]-4-[2(3-dimethylamino-propyl-amino)-4-pyridyl]-2-pyrimidineamine; MS: 464 (M$^+$), 419, 406, $R_f$=0.2 (methylene chloride:methanol:concentrated ammonia solution=80:20:1).

EXAMPLE 8

Analogously to Example 6 there is obtained from 50 mg (0.125 mmol) of N-[3-(1,1,2,2-tetrafluoro-ethoxy)-phenyl]-4-(2-chloro-4-pyridyl)-2-pyrimidineamine and 2 ml of 1,4-diaminobutane N-[3-(1,1,2,2-tetrafluoro-ethoxy)-phenyl-4-[2-(4-amino-butylamino) 4-pyridyl]-2-pyrimidineamine; MS(FAB): 451 (M$^+$+H), $R_f$=0.05 (methylene chloride:methanol:concentrated ammonia solution=80:20:1).

EXAMPLE 9

Analogously to Example 6 there is obtained from 100 mg (0.251 mmol) of N-[3-(1,1,2,2-tetrafluoro-ethoxy)-phenyl]-4-(2-chloro-4-pyridyl)-2-pyrimidineamine dissolved in 1 ml of dimethylformamide and 0.33 ml (2.5 mmol) of 1-(2-amino-ethyl)-piperazine N-[3-(1, 1,2,2-tetrafluoro-ethoxy)-phenyl]-4-{2-[2-(4-formyl-piperazinyl)-ethyl-amino]-4-pyridyl}-2pyrimidineamine; MS (FAB): 520 (M$^+$+H), $R_f$=0.4 (methylene chloride:methanol:concentrated ammonia solution=80:20:1).

EXAMPLE 10

Analogously to Example 6 there is obtained from 174 mg (0.44 mmol) of N-[3-(1,1,2,2-tetrafluoro-ethoxy)-phenyl]-4-(2-chloro-4-pyridyl)-2-pyrimidineamine and 3 ml of 1-(2-amino-ethyl)-piperazine N-[3-(1,1,2-2-tetrafluoro-ethoxy)-phenyl]-4-[2(2 (2-piperazinyl-ethyl-amino)-4-pyridyl]-2-pyrimidineamine; MS (FAB): 492 (M$^+$+H). $R_f$=0.1 (methylene chloride:methanol:concentrated ammonia solution=80:20:1).

EXAMPLE 11

Analogously to Example 6 there is obtained from 100 mg (0.25 1 mmol) of N-[3-(1,1,2,2-tetrafluoro-ethoxy)-phenyl]-4-(2-chloro-4-pyridyl)-2-pyrimidineamine and 2 ml of cis/trans-1,4-diamino-cyclohexane N-[3-(1,1,2,2-tetrafluoro-ethoxy)-phenyl]-4-[2-(cis/trans-4-amino-cyclohexylamino)-4-pyridyl]-2-pyrimidineamine; MS: 476 (M$^+$), 459, 418, $R_f$=0.17 (methylene chloride:methanol:concentrated ammonia solution=80:20:1).

The pure cis-isomer is obtained by repeated chromatographic separation of the cis/trans mixture obtained above in the eluant system methylene chloride/methanol/concentrated ammonia solution (80:20:1).

EXAMPLE 12

Analogously to Example 6 there is obtained from 100 mg (0.251 mmol) of N-[3-(1,1,2,2-tetrafluoro-ethoxy)-phenyl] 4-(2-chloro-4-pyridyl)-2-pyrimidineamine and 0.8 g (5.2 mmol) of cis/trans-4-dimethylamino-cyclohexyl-methylamine N-[-3-(1,1,2,2-tetrafluoro-ethoxy)-phenyl]-4-[2-{(cis/trans-4-dimethylamino-cyclohexyl)-methylamino}-4-pyridyl]-2-pyrimidineamine; MS(FAB): 519 (M$^+$+H), $R_f$=0.2 (methylene chloride:methanol:concentrated ammonia solution=80:20:1).

EXAMPLE 13

Analogously to Example 6 there is obtained from 100 mg (0.251 mmol) of N-[3-(1,1,2,2-tetrafluoro-ethoxy)-phenyl]-4-(2-chloro-5-pyridyl)-2-pyrimidineamine and 0.2 ml of ethylenediamine N-[3-(1,1,2,2-tetrafluoro-ethoxy)-phenyl]-4-[2-(2-aminoethylamino)-5-pyridyl]-2-pyrimidineamine; MS(FAB): 432, $R_f$=0.1 (methylene chloride:methanol:concentrated ammonia solution=90:10:1).

The starting material is obtained in the following manner:

Stage 13.1: 31.91 g (230.3 mmol) of 2-chloro-5-cyanopyridine are placed in 1.6 liters of diethyl ether under nitrogen, and 155 ml (22% in tetrahydrofuran, 456 mmol) of methylmagnesium chloride are added. The red suspension is stirred for 14 h at RT, poured onto 1.6 liters of ice/water and 320 ml of concentrated hydrochloric acid and stirred for 14 h at RT. Extraction with diethyl ether and methylene chloride, drying with MgSO$_4$ and concentration give 5-acetyl-2-chloro-pyridine; $R_f$=0.46 (hexane:ethyl acetate=2:1).

Stage 13.2: 15.4 g (98.7 mmol) of 5-acetyl-2-chloropyridine are stirred for 1 h at 110° with 100 ml of dimethylformamide diethylacetal. After cooling to 0° filtering and drying at 60°, under HV, 3-dimethylamino-1-(2-chloro-5-pyridyl)-2-propen-1-one is obtained; $^1$H-NMR (DMSO): 2.98 (3H,s), 3.2 (3H,s), 5.9 (1H,d), 7.6 (1H,d), 7.8 (1H,d), 8.3 (1H, m), 8.9 (1H,m).

Stage 13.3: 9.22 g (43.8 mmol)of 3-dimethylamino-1-(2-chloro-5-pyridyl)-2-propen-1-one is suspended in 88 ml of 2-propanol. 11 g (43.8 mmol) of 3-(1,1,2,2-tetrafluoro-ethoxy)-phenyl-guanidine nitrate and 1.93 g (48.4 mmol) of sodium hydroxide are added and the reaction mixture is boiled under reflux for 19 h. After cooling to RT, the product is isolated by filtration, washed with 2-propanol and water and dried at 50° under HV. N[3(1,1,2,2-tetrafluoro-ethoxy)-phenyl]-4-(2-chloro-5-pyridyl)-2-pyrimidineamine is obtained; FAB-MS: 399 (M$^+$+H), m.p. 182°–184°.

EXAMPLE 14

Analogously to Example 6 there is obtained from 100 mg (54.2 mmol) of N-[3-(1,1,2,2-tetrafluoro-ethoxy)-phenyl]-4-(2-chloro-5-pyridyl)-2-pyrimidineamine and 2 ml of cis/trans-1,4-diamino-cyclohexane N-[3-(1, 1,2,2-tetrafluoro-ethoxy)-phenyl]-4-[2-(cis/trans-4-amino-cyclohexyl-amino)-5-pyridyl]-2-pyrimidineamine; FAB-MS: 477 (M$^+$+H), $R_f$=0.13 (methylene chloride:methanol:concentrated ammonia solution=80:20:1).

EXAMPLE 15

Analogously to Example 6 there is obtained from 100 mg (0.251 mmol) of N-[3-(1,1,2,2-tetrafluoro-ethoxy)-phenyl] 4-(2-chloro-5-pyridyl)-2-pyrimidineamine, dissolved in 1 ml of dimethylformamide, and 0.33 ml (2.5 mmol) of 1-(2-aminoethyl)-piperazine N-[3-(1,1,2,2-tetrafluoro-ethoxy)-phenyl]-4-[2-{2-(4-formylpiperazinyl)ethylamino}-5-pyridyl]-2-pyrimidineamine; MS(FAB): 520 (M$^+$+H), R$_f$=0.4 (methylene chloride:methanol:concentrated ammonia solution=80:20:1).

EXAMPLE 16

0.58 ml of hydrogen peroxide (30%), 0.16 ml of 1-hexene, 11 mg of sodium carbonate and 2 ml of methanol are added to 50 mg (0.12 mmol) of N-[3-(1,1,2,2-tetrafluoroethoxy)-phenyl]-4-(2-cyano-4-pyridyl)-2-pyrimidineamine and the reaction mixture is stirred for 14 h at RT. The product is isolated by filtration, washed with methanol/water (9:1) and dried to give N-[3-(1,1,2,2-tetrafluoro-ethoxy)-phenyl]-4-(2-carbamoyl-4-pyridyl)-2-pyrimidineamine; m.p. 224°–225°, FAB-MS: 408 (M$^+$+H), 290.

The starting material is obtained in the following manner:

Stage 16.1: 23.6 g (75 mmol) of 3-(1,1,2,2-tetrafluoroethoxy)-phenyl-guanidine nitrate are added to a solution of 13.2 g (75 mmol) of 3-dimethylamino-1-(4-pyridyl)-2-propen-1-one [described in EP-A-0 233 461 ] in 500 ml of isobutanol. After the addition of 4 g (100 mmol) of sodium hydroxide, the reaction mixture is stirred for 3 h at 110°. The suspension is concentrated under reduced pressure and the residue is dissolved in 500 ml of methylene chloride/tetrahydrofuran (1:1) and extracted with 300 ml of water. The organic phase is dried (Na$_2$SO$_4$) and concentrated using a rotovapor. Recrystallisation from diethyl ether/tetrahydrofuran gives N-[3-(1,1,2,2-tetrafluoro-ethoxy-phenyl]-4-(4-pyridyl)-2-pyrimidine-amine; R$_f$=0.9 (methylene chloride:methanol=9:1), FAB-MS:365 (M$^+$+H), m.p. 191°–192°.

Stage 16.2: 500 mg (1.37 mmol)of N-[3-(1,1,2,2-tetrafluoro-ethoxy)-phenyl]-4(4-pyridyl)-2-pyrimidineamine are suspended in 10 ml of methylene chloride; 430 mg (1.37 mmol) of m-chloroperbenzoic acid are added and the reaction mixture is stirred for 4 h at RT. After extraction with water and 2N aqueous sodium hydroxide solution, the organic phase is dried and concentrated using a rotovapor. Chromatography (methylene chloride/methanol=19:1 to 9:1) and subsequent crystallisation (methylene chloride/diethyl ether) give N-[3-(1,1,2,2-tetrafluoro-ethoxy)-phenyl]-4-(N-oxido-4-pyridyl)-2-pyrimidineamine in the form of lemon-yellow crystals; FAB-MS: 381 (M$^+$+H), m.p. 191°–192°.

Stage 16.3: 100 mg (0.26 mmol) of N-[3-(1,1,2,2-tetrafluoro-ethoxy)-phenyl]-4-(N-oxido-4-pyridyl)-2-pyrimidineamine, 90 μl (0.72 mmol) or trimethylsiyl cyanide and 66 μl (0.72 mmol of N,N-dimethyl-carbamoyl chloride are dissolved in 5 ml of acetonitrile and stirred at 60° for 14 h. Concentration under reduced pressure and recrystalisation from tetrahydrofuran/diethyl ether give N-[3-(1,1,2,2-tetrafluoro-ethoxy)phenyl]-4-(2-cyano-4-pyridyl)-2-pyrimidineamine; FAB-MS: 390 (M$^+$+H), R$_f$=0.7 (hexane:ethyl acetate=1:1).

EXAMPLE 17

30 mg (0.077 mmol) of N-[3-(1,1,2,2-tetrafluoro-ethoxy)-phenyl]-4-(2-cyano-4-pyridyl)-2-pyrimidineamine are stirred for 2 hours at 60° in 5 ml of ethanol and 5 ml of 2N sodium hydroxide solution. After acidfying with 4N hydrochloric acid, the product is isolated by filtration, washed with water and dried under HV at 50°. N-[3-1,1,2,2-tetrafluoro-ethoxy)-phenyl]-4-(2-carboxy-4-pyridyl)-2-pyrimidineamine is obtained; m.p. 186°–187°, FAB-MS: 409 (M$^+$+H), 408 (M$^+$), 365.

EXAMPLE 18

Analogously to Example 1 there is obtained from 320 mg (0.83 mmol) of 3-dimethylamino-1-[1-(2-phthalimidoethyl)-3-1H-indoyl]-2-propen-1-one, 40 mg (1.0 mmol) of sodium hydroxide and 260 mg (0.826 mmol) of 3-(1,1,2,2-tetrafluoroethoxy)-phenyl-guanidine nitrate N-[3-(1,1,2,2-tetrafluoro-ethoxy)-phenyl]-4-[1-(2-phthalimido-ethyl)-3-1H-indolyl]-2-pyrimidineamine; m.p. 213°–215°, FAB-MS: 576 (M$^+$+H).

The starting material is obtained in the following manner:

Stage 18.1: 2.5 g (15.7 mmol) of 3-acetyl-1H-indole are dissolved in 100 ml of dimethylformamide, and 0.41 g (15.7 mmol) of sodium hydride and 4.0 g (16 mmol) of N-(2-bromo-ethyl)-phthalimide are added. The reaction mixture is stirred for 14 h at RT and for 3 h at 50°. 20 ml of water are added and the product is isolated by filtration. After drying at 50° under HV, N-[2-(3-acetyl-1H-indol-1-yl)-ethyl]-1H-isoindole-1,3(2H)-dione is obtained; $^1$H-NMR (CDCl$_3$): 2.5 (3H,s), 4.1 (2H,t), 4.45 (2H,t), 7.2–7.9 (8H,m), 8.35 (1H n).

Stage 18.2: 0.61 g (1.8 mmol) of N-[2-(3-acetyl-1H-indol-1-yl)-ethyl]-1H-isoindole-1,3-(2H)-dione is stirred for 170 h in 10 ml of dimethylformamide diethylacetal. After concentration using a rotovapor and chromatography (ethyl acetate:acetone=9:1), 3-dimethyl-amino-1-[1-(2-phthalimido-ethyl)-3-1H-indolyl]-2-propen-1-one is obtained; $^1$H-NMR (CDCl$_3$): 3.0 (6H, s), 4.1 (2H,t) 4.4 (2H,f), 5.6 (1H,d), 7.2–7.9 (9H,m), 8.4 (1H, m).

EXAMPLE 19

Analogously to Example 1 there is obtained from 2.0 g (5 mmol) of 3-dimethylamino-1-[1-(3-phthalimido-propyl)-3-1H-indolyl]-2-propen-1-one, 0.28 g (7 mmol) of sodium hydroxide and 1.56 g (5 mmol) of 3-(1,1,2,2-tetrafluoroethoxy)-phenyl-guanidine nitrate in 100 ml of isobutanol, after 48 h under reflux, N-[3-(1,1,2,2-tetrafluoro-ethoxy)-phenyl]-4-[1-(3-phthalimido-propyl)-3-1H-indolyl]-2-pyrimidineamine; m.p 137°–138°, R$_f$=0.5 (hexane:diethyl ether=1:1).

The starting material is obtained in the following manner:

Stage 19.1:

Analogously to Stage 18.1 there is obtained from 5.0 g (31.4 mmol) of 3-acetyl-1H-indole, 0.83 g (31.4 mmol) of sodium hydried and 6.4 g (31.4 mmol) of N-(3-bromopropyl)-phthalimide N-[3-acetyl-1H-indol-1-yl)-propyl]-1H-isoindole-1,3 (2H)-dione; R$_f$=0.87 (methylene chloride:methanol=9:1).

Stage 19.2

Analogously to Stage 18.2 there is obtained from 2.0 g (5.8 mmol) of N-[3-(3-acetyl-1H-indol-1-yl)-propyl]-1H-isoindole-1,3(2H)-dione and 10 ml of dimethylformamide diethylacetal 3-dimethylamino-1-[1-(3-phthalimido-propyl)-3-1H-indolyl]-2-propen-1-one; R$_f$=0.4 (ethyl acetate:acetone=9:1).

EXAMPLE 20

In a manner analogous to that described above and by simple conversion reactions, known per se, of the products, the following compounds are prepared:

a) N-[3-(1,1,2,2-tetrafluoro-ethoxy)-phenyl]-4-[2-(2-imidazolylethyl-amino)-4-pyridyl]-2-pyrimidineamine, b) N-[3-(1,1,2,2-tetrafluoro-ethoxy)-phenyl]-4-[2-(2-acetamidoethylamino)-4-pyridyl]-2-pyrimidineamine, c) N-[3-(1,1,2,2-tetrafluoro-ethoxy)-phenyl]-4-(2-propylamino-4-pyridyl)-2-pyrimidineamine, d) N-[3-(1,1,2,2-tetrafluoro-ethoxy)-phenyl]-4-(2-amino-4-pyridyl)-2-pyrimidineamine, e) N-[3-(1,1,2,2-tetrafluoro-ethoxy)-phenyl]-4-(2-hydrazino-4-pyridyl)-2-pyrimidineamine, f) N-[3-(1,1,2,2-tetrafluoro-ethoxy)-phenyl]-4-[2-(2-guanidylethylamino)-4-pyridyl]-2-pyrimidineamine, g) N-[3-(1,1,2,2-tetrafluoro-ethoxy)-phenyl]-4-[2-{2-(methylamino-carbonylamino)ethyl}-4-pyridyl]-2-pyrimidineamine, h) N-[3-(1,1,2,2-tetrafluoro-ethoxy)-phenyl]-4-[2-(2-amidino-ethyl)-4-pyridyl]-2-pyrimidineamine, i) N-[3-(1,1,2,2-tetrafluoro-ethoxy)-phenyl]-4-[2-(2-glycylamido-ethyl-amino )-4-pyridyl]-2-pyrimidinea1310 mine, j) N-[3-(1,1,2,2-tetrafluoro-ethoxy)-phenyl]-4-[N-(3-amino-propyl)-3-1H-indolyl]-2-pyrimidineamine, k) N-[3-(1,1,2,2-tetrafluoro-ethoxy)-phenyl]-4-[N-(2-amino-ethyl)-3-1H-indolyl]-2-pyrimidineamine, l) N-[3-(1,1,2,2-tetrafluoro-ethoxy)-phenyl]-4-(3-nitrophenyl)-2-pyrimidineamine, m) N-[3-(1,1,2,2-tetrafluoro-ethoxy)-phenyl]-4-(3-aminocarbonyl-phenyl)-2-pyrimidineamine, n) N-[3-(1,1,2,2-tetrafluoro-ethoxy)-phenyl]-4-[3-{N-(2-amino-ethyl)carbamoyl}-phenyl]-2-pyrimidineamine, o) N-[3-(1,1,2,2-tetrafluoro-ethoxy)-phenyl]-4-[3-{N-(2-hydroxy-ethyl)-carbamoyl}-phenyl]-2-pyrimidineamine, p) N-[3-(1,1,2,2-tetrafluoro-ethoxy)-phenyl]-4-(3-carboxy-phenyl)-2-pyrimidineamine, q) N-(5-benzoylamino-phenyl)-4-[2-(2-amino-ethylamino)-4-pyridyl]-2-pyrimidineamine, r) N-[3-(1,1,2,2-tetrafluoro-ethoxy)-phenyl]-4-(2-hydroxy-4-pyridyl)-2-pyrimidineamine, s) N-[3-(1,1,2,2-tetrafluoro-ethoxy)-phenyl]-4-(2-methoxy-4-pyridyl)-2-pyrimidineamine, t) N-[3-(1,1,2,2-tetrafluoro-ethoxy)-phenyl]-4-[2-{N-(2-amino-ethyl)carbamoyl}-4-pyridyl]-2-pyrimidineamine (see also Example 30), u) N-[3-(1,1,2,2-tetrafluoro-ethoxy)-phenyl]-4-[2-{N-(2-hydroxy-ethyl)carbamoyl}-4-pyridyl]-2-pyrimidineamine (see also Example 28), v) N-[3-(1,1,2,2-tetrafluoro-ethoxy)-phenyl]-4-[2-{N-(3-amino-propyl)carbamoyl}-4-pyridyl]-2-pyrimidineamine (see also Example 31) and w) N-[3-(1,1,2,2-tetrafluoro-ethoxy)-phenyl]-4-[2-{N-(3-hydroxy-propyl)carbamoyl}-4-pyridyl]-2-pyrimidineamine (see also Example 29).

EXAMPLE 21

11.97 g (56.82 mmol)of 3-dimethylamino-1-(2-chloro-4-pyridyl)-2-propen-1-one are suspended in 114 ml of 2-propanol. 14.27 g (56.82 mmol) of 3-(1,1,2,2-tetra-fluoro-ethoxy)-phenyl-guanidine nitrate (for preparation see Stage 1.1) and 2.5 g (62.5 mmol) of sodium hydroxide are added, and the reaction mixture is boiled under reflux for 17 h. After cooling to RT, the product is isolated by filtration, washed with 2-propanol and water and dried at 50° under HV. N-[3-(1,1,2,2-tetrafluoro-ethoxy)phenyl]-4-(2-chloro-4-pyridyl)-2-pyrimidinneamine is obtained; FAB-MS: 399 ($M^+$+ H), m.p. 202°–204°.

The starting material is obtained in the following manner:

Stage 21.1: 24.61 g (177.62 mmol) of 2-chloro-4-cyanopyridine are placed in 1.25 liters of diethyl ether under nitrogen, and 120 ml (22% in tetrahydrofuran, 353 mmol) of methylmagnesium chloride are added. The red suspension is stirred for 40 h at RT, poured onto 1.25 liters of ice/water and 250 ml of 6N hydrochloric acid and stirred for 14 h at RT. Extraction with diethyl ether and methylene chloride, drying with $MgSO_4$ and concentration give 4-acetyl-2-chloro-pyridine; $R_f$=0.5 (methylene chloride:methanol=9:1).

Stage 21.2: 16.2 g (104.2 mmol) of 4-acetyl-2-chloropyridine are stirred for 1 h at 110° with 116 ml of dimethylformamide diethylacetal. After cooling to 0°, filtering and drying at 60° under HV, 3-dimethylamino-1-(2-chloro-4-pyridyl)-2-propen-1-one is obtained; $^1$H-NMR (dimethyl sulfoxide): 2.98 (3H,s), 3.2 (3H,s), 5.9 (1H,d), 7.8 (3H.m), 8.5

EXAMPLE 22

2 g (5.0 mmol)of N-[3-(1,1,2,2-tetrafluoro-ethoxy)-phenyl]-4-(2-chloro-4-pyridyl)-2-pyrimidineamine are stirred for 44 h at 100° in 30 ml of 3-amino-1-propanol. After concentration by evaporation and chromatography (methylene chloride:methanol:conc. ammonia solution=95:5:1), N-[3-(1,1,2,2-tetrafluoro-ethoxy)-phenyl]-4-[2-(3-hydroxypropyl-amino)-4-pyridyl]-2-pyrimidineamine is obtained; m.p. 141°–145°, MS(FAB): 438 ($M^+$+H), $R_f$=0.28 (methylene chloride:methanol:conc. ammonia solution=95:5:1).

EXAMPLE 23

Analogously to Example 22 there is obtained from 100 mg (0.25 mmol) of N-[3-(1,1,2,2-tetrafluoro-ethoxy)-phenyl]-4-(2-chloro-4-pyridyl)-2-Pyrimidineamine and 1.5 ml of ethanolamine N-[3-(1,1,2,2-tetrafluoro-ethoxy)-phenyl]-4-[2-(2-hydroxy-ethyl-amino)-4-4-pyridyl]-2-pyrimidineamine; $R_f$=0.2 (methylene chloride:methanol:conc. ammonia solution=95:5:1), FAB-MS: 424 ($M^+$+H).

EXAMPLE 24

Analogously to Example 22 there is obtained from 100 mg (0.25 mmol) of N-[3-(1,1,2,2-tetrafluoro-ethoxy)-phenyl]-4-(2-chloro-4-pyridyl)-2-pyrimidineamine and 1.5 ml of 3-methoxypropylamine N-[3-(1,1,2,2-tetrafluoro-ethoxy)-phenyl]-4-[2(3-methoxy-propyl-amino)-4-pyridyl]-2-pyrimidineamine; FAB-MS: 452 ($M^+$+H), m.p. 150°–153°.

EXAMPLE 25

In a manner analogous to that described above and by simple conversion reactions, known per se, of the products, the following compounds are prepared:

a) N-[3-(1,1,2,2-tetrafluoro-ethoxy)-phenyl]-4-[2-(2-hydroxy-propyl-amino)-4-pyridyl]-2-pyrimidineamine, b) N-[3-(1,1,2,2-tetrafluoro-ethoxy)-phenyl]-4-[2-(2-carboxy-ethyl-amino)-4-pyridyl]-2-pyrimidineamine (see also Example 27), c) N-[3-(1,1,2,2-tetrafluoro-ethoxy)-phenyl]-4-[2-(2-carbamoyl-ethyl-amino)-4-pyridyl]-2-pyrimidineamine, d) N-[3-(1,1,2,2-tetrafluoro-ethoxy)-phenyl]-4-[2-(2-ethoxycarbonylethylamino)-4-pyridyl]-2-pyrimidineamine, e) N-[3-(1,1,2,2-tetrafluoro-ethoxy)-phenyl]-4-[2-naphthyl]-2-pyrimidineamine (see also Example 34), f) N-[3-(1,1,2,2-tetrafluoro-ethoxy)-phenyl]-4-[1-naphthyl]-2-pyrimidineamine (see also Example 38), g) N-[3-(1,1,2,2-tetrafluoro-ethoxy)-phenyl]-4-[2,4-dichloro-phenyl]-2-pyrimidineamine, h) N-[3-(1,1,2,2-tetrafluoro-ethoxy)-phenyl]-4-[2,5-dichloro-phenyl]-2-pyrimidineamine (see also Example 35), i) N-[3-(1,1,2,2-tetrafluoro-ethoxy)-phenyl]-4-[3,4-dichloro-phenyl]-2-pyrimidineamine (see also Example 36), j) N-[3-(1,1,2,2-tetrafluoro-ethoxy)-phenyl]-4-[2,3,4-trichloro-phenyl]-2-pyrimidineamine (see also Example 37), k) N-[3-(1,1,2,2-tetrafluoro-ethoxy)-phenyl]-4-[2-chlorophenyl]-2-pyrimidineamine (see also Example 33), l) N-[3-(1,1,2,2-tetrafluoro-ethoxy)-phenyl]-4-[3-chlorophenyl]-2-pyrimidineamine, m) N-[3-(1,1,2,2-tetrafluoro-ethoxy)-phenyl]-4-[9-anthracenyl]-2-pyrimidineamine, n) N-[3-(1,1,2,2-tetrafluoro-ethoxy)-phenyl]-4-[2-fluorenyl]-2-pyrimidineamine, o) N-[3-(1,1,2,2-tetrafluoro-ethoxy)-phenyl]-4-[3-(2-amino-ethyl-amino-sulfonyl)phenyl]-2-pyrimidineamine, p) N-[3-(1,1,2,2-tetrafluoro-ethoxy)-phenyl]-4-[3-(1-piperazinyl-sulfonyl)-phenyl]-2-pyrimidineamine, q) N-[3-(1,1,2,2-tetrafluoro-ethoxy)-phenyl]-4-[3-(2-amino-ethyl-amino)-phenyl]-2-pyrimidineamine, r) N-[3-(1,1,2,2-tetrafluoro-ethoxy)-phenyl]-4-[3-(3-amino-propyl-amino)-phenyl]-2-pyrimidineamine s) N-[3-(1,1,2,2-tetrafluoro-ethoxy)-phenyl]-4-[2-{2-(N-hydroxy-carbamoyl)-ethylamino}-4-pyridyl]-2-pyrimidineamine, t) N-[3-(1,1,2,2-tetrafluoro-ethoxy)-phenyl]-4-[2-{3-(N-hydroxy-carbamoyl)-propylamino}-4-pyridyl]-2-pyrimidineamine, u) N-[3-(1,1,2,2-tetrafluoro-ethoxy)-phenyl]-4-[2-(2-dihydroxyphosphoryloxy-ethylamino)-4-pyridinyl]-2-pyrimidineamine and v) N-[3-(1,1,2,2-tetrafluoro-ethoxy)-phenyl]-4-[2-(3-dihydroxyphosphoryloxy-propylamino)-4-pyridyl]-2-pyrimidineamine.

EXAMPLE 26

Analogously to Example 6 them is obtained from 100 mg (0.251 mmol) of N-[3-(1,1,2,2-tetrafluoro-ethoxy)-phenyl]-4-(2-chloro-4-pyridyl)-2-pyrimidineamine and 100 mg (1.33 mmol) of glycine in 3 ml of 1,8-diazabicyclo[5.4.0]undec-7-ene (DBU), after extraction with citric acid and crystallisation from THF/diethyl ether, N-[3-(1,1,2,2-tetrafluoro-ethoxy)-phenyl]-4-[2-(carboxymethyl-amino)-4-pyridyl]-2-pyrimidineamine; m.p. 116°–117°, FAB-MS: 438 (M$^+$+H).

EXAMPLE 27

Analogously to Example 6 there is obtained from 500 mg (1.25 mmol) of N-[3-(1,1,2,2-tetrafluoro-ethoxy)-phenyl]-4-(2-chloro-4-pyridyl)-2-pyrimidineamine and 500 mg (5.6 mmol) of β-alanine in 15 ml of 1,8-diazabicyclo[5.4.0]undec-7-ene (DBU), after extraction with aqueous citric acid and flash chromatography (methylene chloride:methanol:HCOOH=90:10:1), N-[3-(1,1,2,2-tetrafluoro-ethoxy)-phenyl]-4-[2-(2-carboxyethylamino)-4-pyridyl]-2-pyrimidineamine; m.p. 108°–110°, FAB-MS: 452 (M$^+$+H).

EXAMPLE 28

100 mg (0.2 mmol) of N-[3-(1,1,2,2-tetrafluoro-ethoxy)-phenyl]-4-(2-carboxy-4-pyridyl)-2-pyrimidineamine, 73 mg (0.38 mmol) of N-ethyl-N'-(3-dimethylaminopropyl)-carbodiimide hydrochloride and 44 mg (0.38 mmol) of N-hydroxysuccinimide are dissolved in 3 ml of dimethyflormamide and stirred for 2.5 h at RT. The reaction mixture is then added dropwise at 0° over a period of 30 minutes to a solution of 0.75 ml (12.3 mmol) of ethanolamine in 2 ml of DMF. After stirring for 14 h at RT, the reaction mixture is poured into 50 ml of ethyl acetate and extracted with aqueous sodium chloride solution (30 ml) and pH 7 buffer (30 ml), and the organic phase is dried (sodium sulfate) and concentrated. Crystallisation from THF/diethyl ether gives N-[3-(1,1,2,2-tetrafluoro-ethoxy)-phenyl]-4-[2-(2-hydroxyethyl-aminocarbonyl)-4-pyridyl]-2-pyrimidineamine; m.p. 159°, FAB-MS: 452 (M$^+$+H).

EXAMPLE 29

Analogously to Example 28 there is obtained from 100 mg (0.2 mmol) of N-[3-(1,1,2,2-tetrafluoro-ethoxy)-phenyl]-4-(2-carboxy -4-pyridyl)-2-pyrimidineamine, 73 mg (0.38 mmol) of N-ethyl-N'-(3-dimethylaminopropyl)-carbodiimide hydrochloride, 44 mg (0.38 mmol) of N-hydroxysuccmimide and 0.6 ml (8 mmol) of aminopropanol N-[3-(1,1,2,2-tetrafluoro-ethoxy)-phenyl]-4-[2-(3-hydroxy-propyl-aminocarbonyl)-4-pyridyl]-2-pyrimidineamine; m.p. 108°–110°, FAB-MS: 466 (M$^+$+H).

EXAMPLE 30

Analogously to Example 28 there is obtained from 100 mg (0.2 mmol) of N-[3-(1,1,2,2-tetrafluoro-ethoxy)-phenyl]-4-(2-carboxy -4-pyridyl )-2-pyrimidineamine, 73 mg (0.38 mmol) of N-ethyl-N'-(3-dimethylaminopropyl)-carbodiimide hydrochloride, 44 mg (0.38 mmol) of N-hydroxysuccinimide and 0.9 ml of ethylenediamine, after crystallisation from isopropanol/ethanolic hydrochloric acid, N-[3-(1,1,2,2-tetrafluoro-ethoxy)phenyl]-4-[2-(2-amino-ethyl-aminocarbonyl)-4-pyridyl]-2-pyrimidineamine hydrochloride; m.p. 146–153°, FAB-MS: 451 (M$^+$+H).

EXAMPLE 31

Analogously to Example 28 there is obtained from 100 mg (0.2 mmol) of N-[3-(1,1,2,2-tetrafluoro-ethoxy)-phenyl]-4-(2-carboxy-4-pyridyl)-2-pyrimidineamine, 73 mg (0.38 mmol) of N-ethyl-'-(3-dimethylaminopropyl)-carbodiimide hydrochloride, 44 mg (0.38 mmol) of N-hydroxysuccinimide and 0.96 ml (12.9 mmol) of 1,3-diaminopropane, after crystallisation from isopropanoy/ethanolic hydrochloric acid, N-[3-(1,1,2,2-tetrafluoro-ethoxy)phenyl]-4-[2-(3-amino-propyl-aminocarbonyl)-4-pyridyl]-2-pyrimidineamine hydrochloride; m.p. 149°–157°, FAB-MS: 465 (M$^+$+H).

EXAMPLE 32

Analogously to Example 1 there is obtained from 10.99 g (54.9 mmol) of 3-dimethylamino-1-(3-cyano-phenyl)-2-propen-1-one, 13.79 g (54.9 mmol) of 3-(1,1,2,2-tetrafluoroethoxy)-phenyl-guanidine nitrate and 2.42 g (60.4 mmol) of sodium hydroxide N-[3-(1,1,2,2-tetrafluoro-ethoxy)-phenyl]-4-(3-cyano-phenyl)-2-pyrimidineamine; m.p. 180–182°, FAB-MS: 389 (M⁺+H).

The starting material is obtained in the following manner:

Stage 32.1: Analogously to Stage 1.1 there is obtained from 9.70 g (66.8 mmol) of 3-acetyl-benzonitrile and 74.44 ml (434.3 mmol) of N,N-dimethylformamide diethylacetal 3-dimethylamino-1-(3-cyano-phenyl)-2-propen-1-one; ¹H-NMR (DMSO): 2.9 (s,3H), 3.2 (s,3H), 5.9 (d, 1H), 7.6–8.3 (m,5H).

EXAMPLE 33

Analogously to Example 1 there is obtained from 200 mg (0.95 mmol) of 3-dimethylamino-1-(2-chloro-phenyl)-2-propen-1-one, 240 mg (0.95 mmol) of 3-(1,1,2,2-tetrafluoro-ethoxy)-phenyl-guanidine nitrate and 42 mg (1.05 mmol) of sodium hydroxide N-[3-(1,1,2,2-tetrafluoro-ethoxy)-phenyl]-4-(2-chloro-phenyl)-2-pyrimidineamine; m.p. 95°–101°, FAB-MS: 398 (M⁺+H).

The starting material is obtained in the following manner:
Stage 33.1

Analogously to Stage 1.1 there is obtained from 1.0 g (6.5 mmol) of 2-chloroacetophenone and 7.2 ml (42.0 mmol) of N,N-dimethylformamide diethylacetal 3-dimethylamino-1-(2-chloro-phenyl)-2-propen-1-one; ¹H-NMR (DMSO): 2.9 (s, 3H), 3.1 (s,3H), 5.2 (d, 1H), 7.3–7.5 (m,5H).

EXAMPLE 34

Analogously to Example 1 there is obtained from 200 mg (0.89 mmol) of 3-dimethylamino-1-(2-naphthyl)-2-propen-1-one, 223 mg (0.89 mmol) of 3-(1,1,2,2-tetra-fluoro-ethoxy)-phenyl-guanidine nitrate and 39 mg (0.97 mmol) of sodium hydroxide N-[3-(1,1,2,2-tetrafluoro-ethoxy)-phenyl]-4-(2-naphthyl)-2-pyrimidineamine; m.p. 126°–128°, FAB-MS: 414 (M⁺+H).

The starting material is obtained in the following manner:

Stage 34.1: Analogously to Stage 1.1 there is obtained from 1.0 g (5.9 mmol) of 2-methyl naphthyl ketone and 6.5 ml (38.2 mmol) of N,N-dimethylformamide diethylacetal 3-dimethylamino-1-(2-naphthyl)-2-propen-1-one; ¹H-NMR (DMSO): 3.0 (s,3H), 3.2 (s,3H), 6.0 (d, 1H), 7.5–8.1 (m,7H), 8.5 (s, 1H).

EXAMPLE 35

Analogously to Example 1 there is obtained from 200 mg (0.82 mmol) of 3-dimethylamino-1-(2,5-dichloro-phenyl)-2-propen-1-one, 206 mg (0.82 mmol) of 3(1,1,2,2-tetrafluoro-ethoxy)-phenyl-guanidine nitrate and 22.5 mg (0.9 mmol) of sodium hydroxide N-[3-(1,1,2,2-tetrafluoro-ethoxy)-phenyl]-4-(2,5-dichloro-phenyl)-2-pyrimidineamine; m.p. 123°–126°, FAB-MS: 432 (M⁺+H).

The starting material is obtained in the following manner:

Stage 35.1: Analogously to Stage 1.1 there is obtained from 1.0 g (5.3 mmol) of 2,5-dichloro-acetophenone and 5.9 ml (34.4 mmol) of N,N-dimethylformamide diethylacetal 3-dimethylamino-1-(2,5-dichloro-phenyl)-2-propen-1-one; ¹H-NMR (DMSO): 2.9 (s,3H), 3.3 (s,3H), 5.2 (d, 1H), 7.3–7.6 (m,4H).

EXAMPLE 36

Analogously to Example 1 there is obtained from 200 mg (0.82 mmol) of 3-dimethylamino-1-(3,4-dichloro-phenyl)-2-propen-1-one, 206 mg (0.82 mmol) of 3-(1,1,2,2-tetrafluoro-ethoxy)-phenyl-guanidine nitrate and 22.5 mg (0.9 mmol) of sodium hydroxide N-[3-(1,1,2,2-tetrafluoro-ethoxy)-phenyl]-4-(3,4-dichloro-phenyl)-2-pyrimidineamine; m.p. 121°–123°, FAB-MS: 432 (M⁺+H).

The starting material is obtained in the following manner:

Stage 36.1: Analogously to Stage 1.1 there is obtained from 1.0 g (5.3 mmol) of 3,4-dichloro-acetophenone and 5.9 ml (34.4 mmol) of N,N-dimethylformamide diethylacetal 3-dimethylamino-1-(3,4-dichloro-phenyl)-2-propen-1-one; ¹H-NMR (DMSO): 2.9 (s,3H), 3.2 (s,3H), 5.9 (d, 1H), 7.7–8.1 (m,4H).

EXAMPLE 37

Analogously to Example 1 there is obtained from 200 mg (0.89 mmol) of 3-dimethylamino-1-(2,3,4-trichloro-phenyl)-2-propen-1-one, 224.8 mg (0.89 mmol) of 3(1,1,2,2-tetrafluoro-ethoxy)-phenyl-guanidine nitrate and 39.4 mg (0.98 mmol) of sodium hydroxide N-[3-(1,1,2,2-tetrafluoro-ethoxy)-phenyl]-4-(2,3,4-trichloro-phenyl)-2-pyrimidineamine; m.p. 131°–133°, FAB-MS: 466 (M⁺+H).

The starting material is obtained in the following manner:

Stage 37.1: Analogously to Stage 1.1 there is obtained from 1.0 g (4.5 mmol) of 2,3,4-trichloroacetophenone and 7.2 ml (42.0 mmol) of N,N-dimethylformamide diethyhcetal 3-dimethylamino-1-(2,3,4-trichloro-phenyl)-2-propen-1-one; ¹H-NMR (DMSO): 2.9 (s,3H), 3.3 (s,3H), 5.2 (d,1H), 7.2–7.7 (m,3H).

EXAMPLE 38

Analogously to Example 1 there is obtained from 200 mg (0.89 mmol) of 3-dimethylamino-1-(1-naphthyl)-2-propen-1-one, 223 mg (0.89 mmol) of 3-(1,1,2,2-tetrafluoro-ethoxy)-phenyl-guanidine nitrate and 39.1 mg (0.98 mmol) of sodium hydroxide N-[3-(1,1,2,2-tetrafluoro-ethoxy)-phenyl]-4-(1-naphthyl)-2-pyrimidineamine; FAB-MS: 414 (M⁺+H), 296, 205.

The starting material is obtained in the following manner:

Stage 38.1: Analogously to Stage 1.1 there is obtained from 1.0 g (5.88 mmol) of 1-methyl naphthyl ketone and 6.5 ml (38.2 mmol) of N,N-dimethylformamide diethylacetal 3-dimethylamino-1-(1-naphthyl)-2-propen-1-one; $R_f$=0.19 (methylene chloride:methanol=98:2).

EXAMPLE 39

100 mg (0.26 mmol) of N-[3-(1,1,2,2-tetrafluoro-ethoxy)-phenyl]-4-(2-cyano-4-pyridyl)-2-pyrimidineamine and 1.28 ml (1.0M in THF, 1.28 mmol) of diisobutylaluminium hydride/THF solution are stirred for 1 h at −20°. After the addition of 2 ml of methanol, the reaction mixture is heated to RT and the reaction product is isolated by filtration. After concentration under reduced pressure using a rotovapor and chromatography [methylene chloride:methanol:ammonia (conc.)=95:5:]N-[3-(1,1,2,2-tetrafluoro-ethoxy)-phenyl]-4-(2-aminomethyl-4-pyridyl)-2-pyrimidineamine is obtained; m.p. 64°–67°, FAB-MS: 394 (M⁺+H).

EXAMPLE 40

Analogously to Example 1 there is obtained from 5.07 g (23.02 mmol) of 3-dimethylamine-1-(3-nitro-phenyl)-2-propen-1-one, 5.78 g (23.02 mmol) of 3-(1,1,2,2-tetrafluoro-ethoxy)-phenyl-guanidine nitrate and 1.0 g (25.32 mmol) of sodium hydroxide N-[3-(1,1,2,2-tetrafluoro-ethoxy)-phenyl]-4-(3-nitro-phenyl)-2-pyrimidineamine; m.p.

158°–163°, FAB-MS: 409 (M⁺+H).

The starting material is obtained in the following manner:

Stage 40.1: Analogously to Stage 1.1 there is obtained from 4.64 g (27.24 mmol) of 3-nitro-acetophenone and 18.05 ml (105.3 mmol) of N,N-dimethylformamide diethylacetal 3-dimethylamino-1-(3-nitro-phenyl)-2-propen-1-one; $^1$H-NMR (DMSO): 3.0 (s,3H), 3.2 (s,3H), 5.9 (d, 1H), 7.8 (m,2H), 8.3 (m,2H), 8.6 (m,1H).

EXAMPLE 41

Tablets each comprising 20 mg of active ingredient, for example one of the compounds of formula I described in Examples 1–40, are prepared with the following composition in customary manner:

| Composition: | |
| --- | --- |
| active ingredient | 20 mg |
| wheat starch | 60 mg |
| lactose | 50 mg |
| colloidal silica | 5 mg |
| talc | 9 mg |
| magnesium stearate | 1 mg |
| | 145 mg |

Preparation:

The active ingredient is mixed with a portion of the wheat starch, with the lactose and with the colloidal silica, and the mixture is forced through a sieve. A further portion of the wheat starch is made into a paste with 5 times the amount of water on a water bath, and the powder mixture is kneaded with the paste until a slightly plastic mass has been formed.

The plastic mass is pressed through a sieve of approximately 3 mm mesh size and dried, and the resulting dry granules are forced through a sieve again. The remainder of the wheat starch, the talc and the magnesium stearate are admixed and the mixture is compressed to form tablets each weighing 145 mg and having a breaking notch.

EXAMPLE 42

Capsules each comprising 10 mg of active ingredient, for example one of the compounds of formula I described in Examples 1–40, are prepared in customary manner as follows:

| Composition: | |
| --- | --- |
| active ingredient | 2500 mg |
| talc | 200 mg |
| colloidal silica | 50 mg |

Preparation:

The active ingredient is intimately mixed with the talc and the colloidal silica, and the mixture is forced through a sieve of 0.5 mm mesh size and introduced in 11-mg portions into hard gelatin capsules of suitable size.

What is claimed is:

1. An N-phenyl-2-pyrimidineamine derivative of formula I

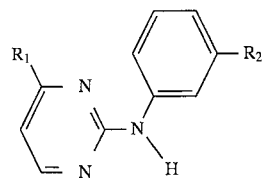

wherein $R_1$ is
- a) naphthyl,
- b) fluorenyl,
- c) anthracenyl or
- d) a substituted cyclic radical, the cyclic radical being bonded to a ring carbon atom in each case and being selected by from phenyl, pyridyl, 1H-indolyl, pyrazinyl, thiazolyl, pyrimidinyl, pyridazinyl and imidazolyl, and the substituents of the above-mentioned phenyl radical being selected from
  - α) hydroxy,
  - β) halogen,
  - γ) nitro,
  - δ) cyano,
  - ε) unsubstituted or halogen-substituted lower alkoxy,
  - ζ) a radical of formula II

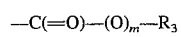

wherein m is 0 or 1 and $R_3$ is hydrogen, benzyl, lower alkyl or amino-lower alkyl wherein the amino group is free, lower alkylated or lower alkoxylated,
- η) a radical of formula III

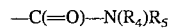

wherein $R_4$ and $R_5$ are each independently of the other hydrogen or unsubstituted or amino- or hydroxy-substituted lower alkyl,
- θ) a radical of formula IV

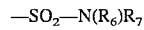

wherein $R_6$ and $R_7$ are each independently of the other hydrogen, lower alkyl or amino-lower alkyl, or wherein $R_6$ and $R_7$ together form the bivalent radical —(CH$_2$)$_2$—NH—(CH$_2$)$_2$—, and
- ι) a radical of formula V

wherein $R_8$ and $R_9$ are each independently of the other lower alkyl, or wherein $R_8$ is hydrogen and $R_9$ is amino or amino-cyclohexyl, or is lower alkyl that is substituted by imidazolyl, guanidyl, lower alkylaminocarbonylamino, amidino, di-lower alkylamino-cyclohexyl, piperazinyl, carboxy, lower alkoxycarbonyl, carbamoyl, N-hydroxy-carbamoyl, hydroxy, lower alkoxy, dihydroxyphosphoryloxy or by formylpiperazinyl, and the substituents of the other above-mentioned cyclic radicals pyridyl, 1H-indolyl, pyrazinyl, thiazolyl, pyrimidinyl, pyridazinyl and imidazolyl being selected from a) hydroxy,
b) halogen,
c) cyano,
d) amino-lower alkyl,
e) unsubstituted or halogen-substituted lower alkoxy,
f) phthalimido-substituted lower alkyl,
g) a radical of the above-mentioned formulae II, III or IV and
h) a radical of formula VI $$-N(R_{10})R_{11} \quad (VI)$$

wherein $R_{10}$ and $R_{11}$ are each independently of the other hydrogen or lower alkyl, or wherein $R_{10}$ is hydrogen and $R_{11}$ is amino or amino-cyclohexyl, or is lower alkyl substituted by amino, lower alkylamino, di-lower alkylamino, lower alkanoylamino, imidazolyl, guanidyl, lower alkylamino-carbonylamino, amidino, di-lower alkylamino-cyclohexyl, piperazinyl, formylpiperazinyl, carboxy, lower alkoxycarbonyl, carbamoyl, N-hydroxy-carbamoyl, hydroxy, lower alkoxy, dihydroxyphosphoryloxy or by glycylamido; and $R_2$ is nitro, fluorine-substituted lower alkoxy or a radical of formula VII $$-N(R_{12})-C(=X)-(Y)_n-R_{13} \quad (VII)$$

wherein $R_{12}$ is hydrogen or lower alkyl,

X is oxo, thio, imino, N-lower alkyl-imino, hydroximino or O-lower alkyl-hydroximino, Y is oxygen or the group NH, n is 0 or 1, and $R_{13}$ is
  a) an unsubstituted aliphatic hydrocarbon radical having 5 to 22 carbon atoms,
  b) phenyl or naphthyl each of which is unsubstituted or substituted by α) cyano, β) lower alkyl that is unsubstituted or substituted by hydroxy, amino or by 4-methyl-piperazinyl, γ) trifluoromethyl, δ) hydroxy, ε) lower alkoxy, ζ) lower alkanoyloxy, η) halogen, θ) amino, ι) lower alkylamino, χ) di-lower alkylamino, λ) lower alkanoylamino, μ) benzoylamino, ν) carboxy, or ξ) lower alkoxycarbonyl,
  c) lower alkyl which is substituted by a phenyl or naphthyl radical as defined in the preceding paragraph b),
  d) a 5- or 6-membered cycloalkyl radical,
  e) lower alkyl which is substituted by a 5- or 6-membered cycloalkyl radical,
  f) a thienyl or 2-, 3- or 4-pyridyl radical or
  g) lower alkyl substituted by a thienyl or a 2-, 3- or 4-pyridyl radical,
or a salt of such a compound having at least one salt-forming group.

2. A compound according to claim 1 of formula I, wherein the substituted cyclic radical $R_1$ is selected from phenyl, pyridyl and 1H-indolyl, the phenyl substituents being selected from
a) unsubstituted or fluorine-substituted lower alkoxy,
b) halogen,
c) nitro,
d) a radical of formula II wherein
  m is 1 and
  $R_3$ is hydrogen, and
e) a radical of formula III wherein
  $R_4$ is hydrogen and
  $R_5$ is hydrogen or amino- or hydroxy-substituted lower alkyl, and the substituents of the other above-mentioned cyclic radicals being selected from
a) hydroxy,
b) halogen,
c) lower alkoxy,
d) amino- or phthalimido-substituted lower alkyl,
e) a radical of formula II wherein
  m is 1 and
  $R_3$ is hydrogen,
f) a radical of formula III wherein
  $R_4$ is hydrogen and
  $R_5$ is hydrogen or amino- or hydroxy-substituted lower alkyl, and
g) a radical of formula VI wherein
  $R_{10}$ is hydrogen and
  $R_{11}$ is amino or amino-cyclohexyl, or is lower alkyl substituted by amino, di-lower alkylamino, lower alkanoylamino, imidazolyl, guanidyl, lower alkylamino-carbonylamino, amidino, di-lower alkylamino-cyclohexyl, piperazinyl, formyl-piperazinyl or by glycylamido; and
  $R_2$ is fluorine-substituted lower alkoxy or a radical of formula VII wherein
  $R_{12}$ is hydrogen,
  X is oxo,
  n is 0 and
  $R_{13}$ is phenyl,
or a salt of such a compound having at least one salt-forming group.

3. A compound according to claim 1 of formula I, wherein $R_1$ is naphthyl, 9-anthracenyl, 2-fluorenyl or a substituted cyclic radical selected from phenyl, pyridyl and 1H-indolyl, the phenyl substituents being selected from
a) $C_{1-2}$ alkoxy,
b) chlorine,
c) trifluoromethoxy,
d) a radical of formula II wherein
  m is 1 and
  $R_3$ is hydrogen,
from a radical of formula III wherein
  $R_4$ is hydrogen and
  $R_5$ is hydrogen or $C_{2-3}$alkyl substituted in the ω-position by amino or by hydroxy,
e) a radical of formula IV wherein
  $R_6$ is hydrogen and
  $R_7$ is 2-amino-ethyl, or
  $R_6$ and $R_7$ together form the bivalent radical $-(CH_2)_2-NH-(CH_2)_2-$, and
f) a radical of formula V wherein
  $R_8$ is hydrogen and
  $R_9$ is $C_{2-3}$alkyl substituted in the ω-position by amino,
the pyridyl substituents being selected from
a) hydroxy,
b) chlorine,
c) methoxy,
d) a radical of formula II wherein
  m is 1 and
  $R_3$ is hydrogen,
e) a radical of formula III wherein

39

R$_4$ is hydrogen and
R$_5$ is hydrogen or C$_{2-3}$alkyl substituted in the ω-position by amino or by hydroxy,
f) a radical of formula IV wherein
R$_6$ is hydrogen and
R$_7$ is 2-amino-ethyl, or
R$_6$ and R$_7$ together form the bivalent radical -(CH$_2$)$_2$—NH—(CH$_2$)$_2$—, and
g) a radical of formula VI wherein
R$_{10}$ is hydrogen and
R$_{11}$ is hydrogen, C$_{1-4}$alkyl, amino, 4-amino-cyclohexyl or 2-hydroxy-propyl, or is C$_{1-4}$ alkyl substituted in the co-position by amino, dimethylamino, acetylamino, imidazol-1-yl, guanidyl, methylamino-carbonylamino, amidino, 4-dimethylamino-cyclohexyl, piperazin-1-yl, 4-formyl-- piperazin-1-yl, carboxy, ethoxycarbonyl, carbamoyl, N-hydroxy-carbamoyl, hydroxy, methoxy, dihydroxyphosphoryloxy or by glycylamido, and the 1H-indolyl substituents being selected from C$_{2-3}$ alkyl substituted in the ω-position by amino or by phthalimido; and
R$_2$ is 1,1,2,2-tetrafluoro-ethoxy or a radical of formula VII wherein
R$_{12}$ is hydrogen,
X is oxo,
n is 0 and
R$_{13}$ is phenyl,
or a salt of such a compound having at least one salt-forming group.

4. A compound according to claim 1 of formula I, wherein R$_1$ is a substituted cyclic radical selected from phenyl, pyridyl and 1H-indolyl, the phenyl substituents being selected from
a) C$_{1-2}$ alkoxy,
b) chlorine,
c) trifluoromethoxy,
d) a radical of formula II wherein
m is 1 and
R$_3$ is hydrogen, and
e) a radical of formula III wherein
R$_4$ is hydrogen and
R$_5$ is hydrogen or C$_{2-3}$alkyl substituted in the ω-position by amino or by hydroxy,
the pyridyl substituents being selected from
a) hydroxy,
b) chlorine,
c) methoxy,
d) a radical of formula II wherein
m is 1 and
R$_3$ is hydrogen,
e) a radical of formula III wherein
R$_4$ is hydrogen and
R$_5$ is hydrogen or C$_{2-3}$ alkyl substituted in the ω-position by amino or by hydroxy, and
f) a radical of formula VI wherein
R$_{10}$ is hydrogen and
R$_{11}$ is amino or 4-amino-cyclohexyl, or is C$_{1-4}$alkyl substituted in the ω-position by amino, dimethylamino, acetylamino, imidazolo-1-yl, guanidyl, methylamino-carbonylamino, amidino, 4-dimethylamino-cyclohexyl, piperazin-1-yl, 4-formyl-piperazin-1-yl or by glycylamido, and the 1H-indolyl substituents being selected from C$_{2-3}$alkyl substituted in the ω-position by amino or by phthalimido; and

40

R$_2$ is 1,1,2,2-tetrafluoro-ethoxy or a radical of formula VII wherein
R$_{12}$ is hydrogen,
X is oxo,
n is 0 and
R$_{13}$ is phenyl,
or a salt of such a compound having at least one salt-forming group.

5. A compound according to claim 1 of formula I, wherein R$_1$ is naphthyl or a substituted cyclic radical selected from phenyl, pyridyl and 1H-indolyl, the phenyl substituents being selected from
a) C$_{1-2}$alkoxy,
b) chlorine,
c) trifluoromethoxy,
d) nitro,
e) cyano,
f) a radical of formula II wherein
m is 1 and
R$_3$ is hydrogen, and
g) a radical of formula III wherein
R$_4$ is hydrogen and
R$_5$ is hydrogen or C$_{2-3}$alkyl substituted in the ω-position by amino or by hydroxy,
the pyridyl substituents being in the ortho-position with respect to the pyridine nitrogen and being selected from
a) hydroxy,
b) chlorine,
c) methoxy,
d) aminomethyl,
e) a radical of formula II wherein
m is 1 and
R$_3$ is hydrogen,
f) a radical of formula III wherein
R$_4$ is hydrogen and
R$_5$ is hydrogen or C$_{2-3}$alkyl substituted in the ω-position by amino or by hydroxy, and
g) a radical of formula VI wherein
R$_{10}$ is hydrogen and
R$_{11}$ is amino or 4-amino-cyclohexyl, or is C$_{1-4}$alkyl substituted in the ω-position by amino, dimethylamino, acetylamino, imidazol-1-yl, guanidyl, methylamino-carbonylamino, amidino, 4-dimethylamino-cyclohexyl, piperazin-1-yl, 4-formyl-piperazin-1-yl, glycylamido or by carboxy,
and the 1H-indolyl substituents being selected from C$_{2-3}$alkyl substituted in the ω-position by amino or by phthalimido; and
R$_2$ is 1,1,2,2-tetrafluoro-ethoxy or a radical of formula VII wherein
R$_{12}$ is hydrogen,
X is oxo,
n is 0 and
R$_{13}$ is phenyl,
or a salt of such a compound having at least one salt-forming group.

6. A compound of formual I according to claim 1 or a pharmaceutically acceptable salt of such a compound having at least one salt-foming group, selected from
N-[3-(1,1,2,2-tetrafluoro-ethoxy)-phenyl]-4-(3,4,5-trimethoxyphenyl)-2-pyrimidineamine,
N-[3-(1,1,2,2-tetrafluoro-ethoxy)-phenyl]-4-(3-methoxyphenyl)-2-pyrimidineamine,
N-[3-(1,1,2,2-tetrafluoro-ethoxy)-phenyl]-4-(4-chlorophenyl)-2-pyrimidineamine, N-[3-(1,1,2,2-tetrafluoro-ethoxy)-phenyl]-4-(3-ethoxy-phenyl)-2-pyrimidineamine,
N-[3-(1,1,2,2-tetrafluoro-ethoxy)-phenyl]-4-(3-trifluoromethoxy-phenyl)-2-pyrimidineamine,
N-3-(1,1,2,2-tetrafluoro-ethoxy)-phenyl]-4-[2-(2-amino-ethyl-amino)-4-pyridyl]-2-pyrimidineamine,
N-[3-(1,1,2,2-tetrafluoro-ethoxy)-phenyl]-4-[2-(3-dimethylamino-propyl-amino)-4-pyridyl]-2-pyrimidineamine,
N-[3-(1,1,2,2,-tetrafluoro-ethoxy)phenyl]-4-[2-(4-aminobutylamino)-4-pyridyl]-2-pyrimidineamine,
N-[3-(1,1,2,2-tetrafluoro-ethoxy)-phenyl]-4-{2-[2-(4-formyl-piperazinyl)-ethyl-amino]-4-pyridyl}-2-pyrimidineamine,
N-[3-(1,1,2,2-tetrafluoro-ethoxy)-phenyl]-4-[2-(2-piperazinyl-ethyl-amino)-4-pyridyl]-2-pyrimidineamine,
N-[3-(1,1,2,2-tetrafluoro-ethoxy)-phenyl]-4-[2-(cis-trans-4-amino-cyclohexylamino)-4-pyridyl]-2-pyrimidineamine,
N-[3-(1,1,2,2-tetrafluoro-ethoxy)-phenyl]-4-[2-(cis-4-amino-cyclohexylamino)-4-pyridyl]-2-pyrimidineamine,
N-[3-(1,1,2,2-tetrafluoro-ethoxy)-phenyl]-4-[2-{(cis/trans-4-dimethylamino-cyclohexyl)-methylamino }-4-pyridyl]-2-pyrimidineamine,
N-[3-(1,1,2,2-tetrafluoro-ethoxy)-phenyl]-4-[2-(2-amino-ethyl-amino)-5-pyridyl]-2-pyridmidineamine,
N-[3-(1,1,2,2-tetrafluoro-ethoxy)-phenyl]-4-[2-(cis/trans-4-amino-cyclohexyl-amino)-5-pyridyl]-2-pyrimidineamine,
N-[3-(1,1,2,2-tetrafluoro-ethoxy)-phenyl]-4-[2-{2-(4-formylpiperazinyl)-ethyl-amino}-5-pyridyl]-2-pyrimidineamine,
N-[3-(1,1,2,2-tetrafluoro-ethoxy)-phenyl]-4-(2-carbamoyl-4-pyridyl)-2-pyrimidineamine,
N-[3-(1,1,2,2-tetrafluoro-ethoxy)-phenyl]-4-(2-carboxy-4-pyridyl)-2-pyrimidineamine,
N-[3-(1,1,2,2-tetrafluoro-ethoxy)-phenyl]-4-[1-(2-phthalimido-ethyl)-3-1H-indolyl]-2-pyrimidineamine,
N-[3-(1,1,2,2-tetrafluoro-ethoxy)-phenyl]-4-[1-(3-phthalimido-propyl)-3-1H-indolyl]-2-pyrimidineamine,
N-[3-(1,1,2,2-tetrafluoro-ethoxy)-phenyl]-4-[2-(2-imidazolylethyl-amino)-4-pyridyl]-2-pyrimidineamine,
N-[3-(1,1,2,2-tetrafluoro-ethoxy)-phenyl]-4-[2-(2-acetamidoethylamino)-4-pyridyl]-2-pyrimidineamine,
N-[3-(1,1,2,2-tetrafluoro-ethoxy)-phenyl]-4-(2-propylamino-4-pyridyl)-2-pyrimidineamine,
N-[3-(1,1,2,2-tetrafluoro-ethoxy)-phenyl]-4-(2-amino-4-pyridyl)-2-pyrimidineamine,
N-[3-(1,1,2,2-tetrafluoro-ethoxy)-phenyl]-4-(2-hydrazino-4-pyridyl)-2-pyrimidineamine,
N-[3-(1,1,2,2-tetrafluoro-ethoxy)-phenyl]-4-[2-(2-guanidylethylamino-4-pyridyl]-2-pyrimidineamine,
N-[3-(1,1,2,2-tetrafluoro-ethoxy)-phenyl]-4-[2-{2-(methylamino-carbonylamino)ethyl}-4-pyridyl]-2-pyrimidineamine,
N-[3-(1,1,2,2-tetrafluoro-ethoxy)-phenyl]-4-[2-(2-amidino-ethyl)-4-pyridyl]-2-pyrimidineamine,
N-[3-(1,1,2,2,-tetrafluoro-ethoxy)-phenyl]-4-[2-(2-glycylamido-ethyl-amino)-4-pyridyl]-2-pyrimidineamine,
N-[3-(1,1,2,2-tetrafluoro-ethoxy)-phenyl]-4-[N-(3-amino-propyl)-3-1H-indolyl]-2-pyrimidineamine,
N-[3-(1,1,2,2-tetrafluoro-ethoxy)-phenyl]-4-[N-(2-amino-ethyl)-3-1H-indolyl]-2-pyrimidineamine
N-[3-(1,1,2,2-tetrafluoro-ethoxy)-phenyl]-4-(3-nitro-phenyl)-2-pyrimidineamine,
N-[3-(1,1,2,2-tetrafluoro-ethoxy)-phenyl]-4-(3-aminocarbonyl-phenyl)-2-pyrimidineamine,
N-[3-(1,1,2,2-tetrafluoro-ethoxy)-phenyl]-4-[3-{N-(2-amino-ethyl)carbamoyl}-phenyl]-2-pyrimidineamine,
N-[3-(1,1,2,2-tetrafluoro-ethoxy)-phenyl]-4-[3-{N-(2-hydroxy-ethyl)-carbamoyl}-phenyl]-2-pyrimidineamine,
N-[3-(1,1,2,2-tetrafluoro-ethoxy)-phenyl]-4-(3-carboxyphenyl)-2-pyrimidineamine,
N-(5-benzoylamino-phenyl)-4-[2-(2-amino-ethyl-amino)-4-pyridyl]-2-pyrimidineamine,
N-[3-(1,1,2,2-tetrafluoro-ethoxy)-phenyl]-4-(2-hydroxy-4-pyridyl)-2-pyrimidineamine,
N-[3-(1,1,2,2-tetrafluoro-ethoxy)-phenyl]-4-(2-methoxy-4-pyridyl)-2-pyrimidineamine,
N-[3-(1,1,2,2-tetrafluoro-ethoxy)-phenyl]-4-[2-{N-(2-amino-ethyl )carbamoyl}-4-pyridyl]-2-pyrimidineamine,
N-[3-(1,1,2,2-tetrafluoro-ethoxy)-phenyl]-4-[2-{N-(2-hydroxy-ethyl)carbamoyl}-4-pyridyl]-2-pyrimidineamine,
N-[3-(1,1,2,2-tetrafluoro-ethoxy)-phenyl]-4-[2-{N-(3-amino-propyl)carbamoyl}-4-pyridyl]-2-pyrimidineamine,
N-[3-(1,1,2,2-tetrafluoro-ethoxy)-phenyl]-4-[2-{N-(3-hydroxy-propyl)carbamoyl}-4-pyridyl]-2-pyrimidineamine,
N-[3-(1,1,2,2-tetrafluoro-ethoxy)-phenyl]-4-(2-chloro-4-pyridyl)-2-pyrimidineamine,
N-[3-(1,1,2,2-tetrafluoro-ethoxy)-phenyl]-4-[2-(3-hydroxy-propyl-amino)-4-pyridyl]-2-pyrimidineamine,
N-[3-(1,1,2,2-tetrafluoro-ethoxy)-phenyl]-4-(2-hydroxyethyl-amino)-4-pyrdyl-2-pyrimidineamine,
N-[3-(1,1,2,2-tetrafluoro-ethoxy)-phenyl]-4-[2-(3-methoxy-propyl-amino)-4-pyridyl]-2-pyrimidineamine,
N-[3-(1,1,2,2-tetrafluoro-ethoxy)-phenyl]-4-[2-(2-hydroxy-propyl-amino )-4-pyridyl]-2-pyrimidineamine,
N-[3-(1,1,2,2-tetrafluoro-ethoxy)-phenyl]-4-[2-(2-carboxy-ethyl-amino)-4-pyridyl]-2-pyrimidineamine,
N-[3-(1,1,2,2-tetrafluoro-ethoxy)-phenyl]-4-[2-(2-carbamoyl-ethyl-amino)-4-pyridyl]-2-pyrimidineamine,
N-[3-(1,1,2,2-tetrafluoro-ethoxy)-phenyl]-4-[2-(2-ethoxycarbonylethylamino)-4-pyridyl]-2-pyrimidineamine,
N-[3-(1,1,2,2-tetrafluoro-ethoxy)-phenyl]-4-[2-naphthyl]-2-pyrimidineamine,
N-[3-(1,1,2,2-tetrafluoro-ethoxy)-phenyl]-4-[1-naphthyl]-2-pyrimidineamine,
N-[3-(1,1,2,2-tetrafluoro-ethoxy)-phenyl]-4-[2,4-dichloro-phenyl]-2-pyrimidineamine,
N-[3-(1,1,2,2-tetrafluoro-ethoxy)-phenyl]-4-[2,5-dichloro-phenyl]-2-pyrimidineamine,
N-[3-(1,1,2,2-tetrafluoro-ethoxy)-phenyl]-4-[3,4-dichloro-phenyl]-2-pyrimidineamine,
N-[3-(1,1,2,2-tetrafluoro-ethoxy)-phenyl]-4-[2,3,4-trichloro-phenyl]-2-pyrimidineamine,
N-[3-(1,1,2,2-tetrafluoro-ethoxy)-phenyl]-4-[2-chlorophenyl]-2-pyrimidineamine,
N-[3-(1,1,2,2-tetrafluoro-ethoxy)-phenyl]-4-[3-chlorophenyl]-2-pyrimidineamine, N-[3-(1,1,2,2-tetrafluoro-ethoxy)-phenyl]-4-[9-anthracenyl]-2-pyrimidineamine, N-[3-(1,1,2,2-tetrafluoro-ethoxy)-phenyl]-4-[2-fluorenyl]-2-pyrimidineamine, N-[3-(1,1,2,2-tetrafluoro-ethoxy)-phenyl]-4-[3-(2-aminoethyl-amino-sulfonyl)-phenyl]-2-pyrimidineamine, N-[3-(1,1,2,2-tetrafluoro-ethoxy)-phenyl]-4-[3-(1-piperazinyl-sulfonyl)-phenyl]-2-pyrimidineamine, N-[3-(1,1,2,2-tetrafluoro-ethoxy)-phenyl]-4-[3-(2-aminoethyl-amino)-phenyl]-2-pyrimidineamine, N-[3-(1,1,2,2-tetrafluoro-ethoxy)-phenyl]-4-[3-(3-aminopropyl-amino)-phenyl]-2-pyrimidineamin N-[3-(1,1,2,2-tetrafluoro-ethoxy)-phenyl]-4-[2-{2-(N-hydroxy-carbamoyl)-ethyl-amino}-4-pyridyl]-2-pyrimidineamine, N-[3-(1,1,2,2-tetrafluoro-ethoxy)-phenyl]-4-[2-{3-(N-hydroxy-carbamoyl)-propylamino}-4-pyridyl]-2-pyrimidineamine, N-[3-(1,1,2,2-tetrafluoro-ethoxy)-phenyl]-4-[2-(2-dihydroxyphosphoryloxy-ethyl-amino)-4-pyridyl]-2-pyrimidineamine, N-[3-(1,1,2,2-tetrafluoro-ethoxy)-phenyl]-4-[2-(3-dihydroxyphosphoryloxy-propylamino)-4-pyridyl]-2-pyrimidineamine, N-[3-(1,1,2,2-tetrafluoro-ethoxy)-phenyl]-4-[2(carboxymethyl-amino)-4-pyridyl]-2-pyrimidineamine, N-[3-(1,1,2,2-tetrafluoro-ethoxy)-phenyl]-4-[2-(2-carboxyethylamino)-4-pyridyl]-2-pyridmidineamine, N-[3-(1,1,2,2-tetrafluoro-ethoxy)-phenyl]-4-[2-(2-hydroxy-ethyl-aminocarbonyl)-4-pyridyl]-2-pyrimidineamine, N-[3-(1,1,2,2-tetrafluoro-ethoxy)-phenyl]-4-[2-(3-hydroxy-propyl-aminocarbonyl)-4-pyridyl]-2-pyrimidineamine, N-[3-(1,1,2,2-tetrafluoro-ethoxy)-phenyl]-4-[2-(2-aminoethyl-aminocarbonyl)-4-pyridyl]-2-pyrimidineamine, N-[3-(1,1,2,2-tetrafluoro-ethoxy)-phenyl]-4-[2-(3-aminopropyl-aminocarbonyl)-4-pyridyl]-2-pyrimidineamine, N-[3-(1,1,2,2-tetrafluoro-ethoxy)-phenyl]-4-(3-cyanophenyl)-2-pyrimidineamine, N-[3-(1,1,2,2-tetrafluoro-ethoxy)-phenyl]-4-(2-chlorophenyl)-2-pyrimidineamine, N-[3-(1,1,2,2-tetrafluoro-ethoxy)-phenyl]-4-(2-naphthyl)-2-pyrimidineamine, N-[3-(1,1,2,2-tetrafluoro-ethoxy)-phenyl]-4-(2,5-dichloro-phenyl)-2-pyrimidineamine, N-[3-(1,1,2,2-tetrafluoro-ethoxy)-phenyl]-4-(3,4-dichloro-phenyl)-2-pyrimidineamine, N-[3-(1,1,2,2-tetrafluoro-ethoxy)-phenyl]-4-(2,3,4-trichloro-phenyl)-2-pyrimidineamine, N-[3-(1,1,2,2-tetrafluoro-ethoxy)-phenyl]-4-(1-naphthyl)-2-pyrimidineamine, N-[3-(1,1,2,2-tetrafluoro-ethoxy)-phenyl]-4-(2-aminomethyl-4-pyridyl)-2-pyrimidineamine and N-[3-(1,1,2,2-tetrafluoro-ethoxy)-phenyl]-4-(3-nitro-phenyl)-2-pyrimidineamine, and from pharmaceutically acceptable salts of such compounds having at least one salt-forming group.

7. A pharmaceutical composition for the treatment of tumours responsive to inhibition of protein kinase C, EGF-receptor-specific tyrosine protein kinase or $p34^{cdc2}$/cyclineB$^{cdc13}$kinase, in warm-blooded animals including humans, comprising a dose effective against tumours responsive to inhibition of protein kinase C, EGF-receptor-specific tyrosine protein kinase or $p34^{cdc2}$/cyclineB$^{cdc13}$kinase of a compound of formula I according to claim 1 or a pharmaceutically acceptable salt of such a compound having at least one salt-forming group together with a pharmaceutical carrier.

8. A method of treating a warm-blooded animal including a human, which comprises administering to such a warm-blooded animal suffering from a tumour disease responsive to inhibition of protein kinase C, EGF-receptor-specific tyrosine protein kinase or $p34^{cdc2}$/cyclineB$^{cdc13}$kinase a dose effective against tumours which are responsive to inhibition of protein kinase C, EGF-receptor-specific tyrosine protein kinase or $p34^{cdc2}$cyclineB$^{cdc13}$kinase, of a compound of formula I according to claim 1 or of a pharmaceutically acceptable salt of such a compound having at least one salt-forming group.

* * * * *